United States Patent
Sekino et al.

(10) Patent No.: US 6,270,497 B1
(45) Date of Patent: Aug. 7, 2001

(54) HIGH-FREQUENCY TREATMENT APPARATUS HAVING CONTROL MECHANISM FOR INCISING TISSUE AFTER COMPLETION OF COAGULATION BY HIGH-FREQUENCY TREATMENT TOOL

(75) Inventors: Naomi Sekino, Hachioji; Koji Iida, Sagamihara; Norihiko Hareyama, Hachioji; Shinji Hatta, Hachioji; Koji Yamauchi, Hachioji, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/324,194

(22) Filed: Jun. 2, 1999

(30) Foreign Application Priority Data

Aug. 27, 1998 (JP) .................................. 10-241945
Mar. 19, 1999 (JP) .................................. 11-076715

(51) Int. Cl.[7] .................................................. A61B 18/18
(52) U.S. Cl. .............................. 606/42; 606/45; 606/49
(58) Field of Search ........................ 606/40, 41, 42, 606/45, 46, 50–52

(56) References Cited

U.S. PATENT DOCUMENTS 5,190,541 * 3/1993 Abele et al. ........................ 606/46
5,269,780  12/1993 Roos .
5,445,638 * 8/1995 Rydell et al. ........................ 606/51
6,024,741 * 2/2000 Williamson, IV et al. .......... 606/40
6,110,171 * 8/2000 Rydell .................................. 606/51
6,113,598 * 9/2000 Baker .................................. 606/51

FOREIGN PATENT DOCUMENTS 11-267132  10/1999 (JP) .

* cited by examiner

Primary Examiner—Michael Peffley
(74) Attorney, Agent, or Firm—Frishauf, Holtz, Goodman, Langer & Chick, P.C.

(57) ABSTRACT

A high-frequency treatment apparatus has a high-frequency treatment tool having, at its distal end portion, a treatment portion for coagulating or incising tissue. A high-frequency output power supply unit is electrically connected to the high-frequency treatment tool to selectively generate a high-frequency coagulation output for coagulating tissue and a high-frequency incision output for incising the tissue on the basis of a signal generated upon manipulating a manipulation portion. The manipulation portion has a control mechanism for causing the high-frequency treatment tool to incise tissue after coagulation of the tissue by the high-frequency treatment tool is completed.

4 Claims, 15 Drawing Sheets

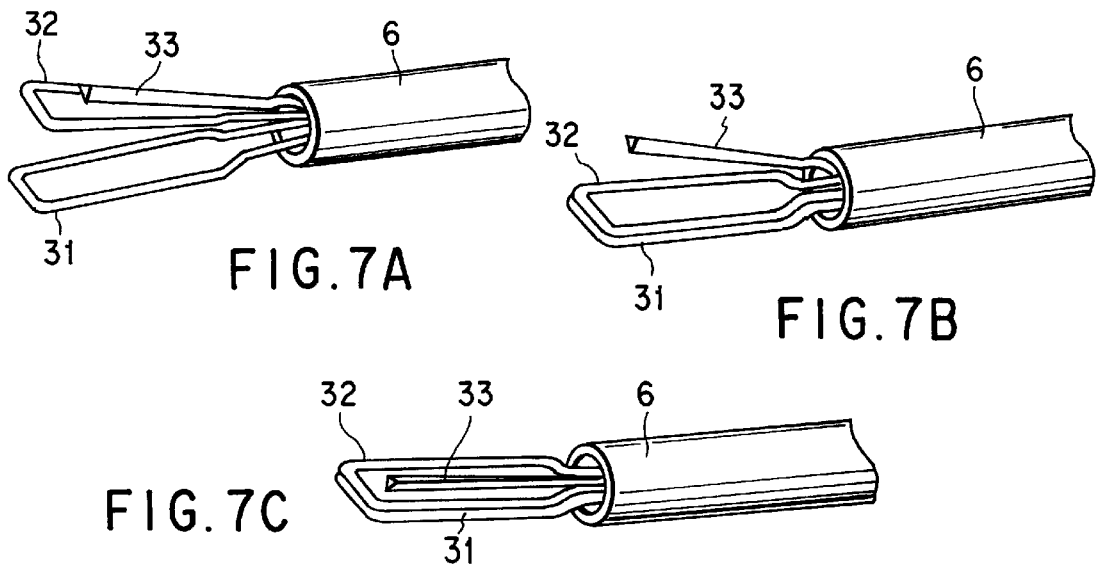
FIG.7A
FIG.7B
FIG.7C
FIG.8
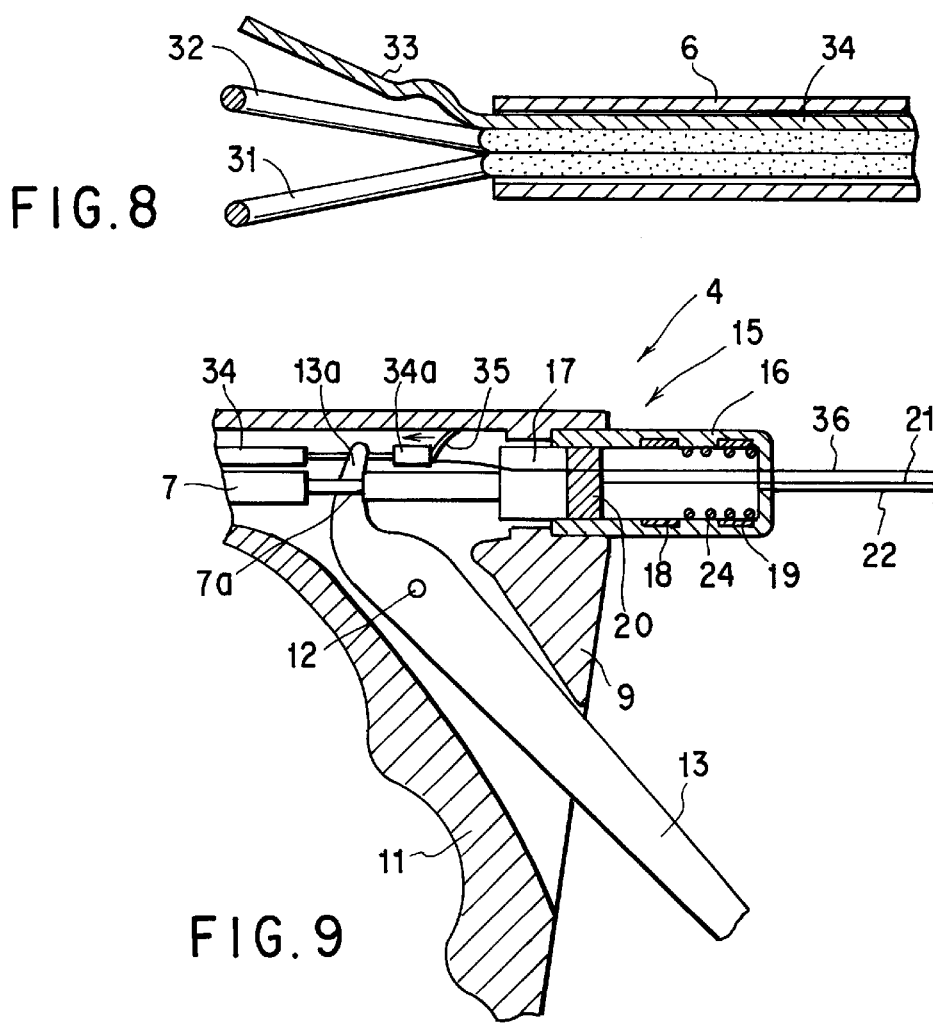
FIG.9

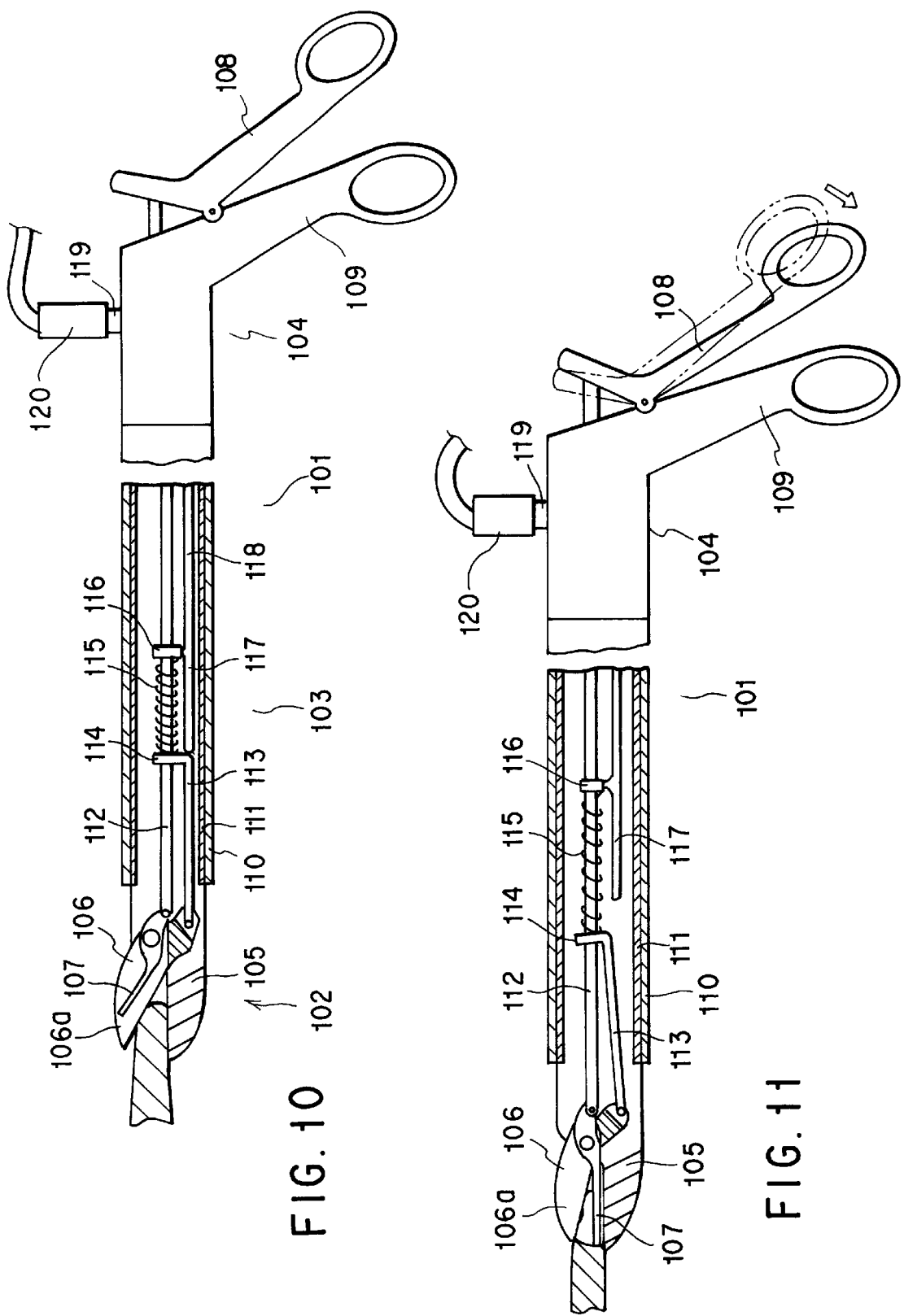

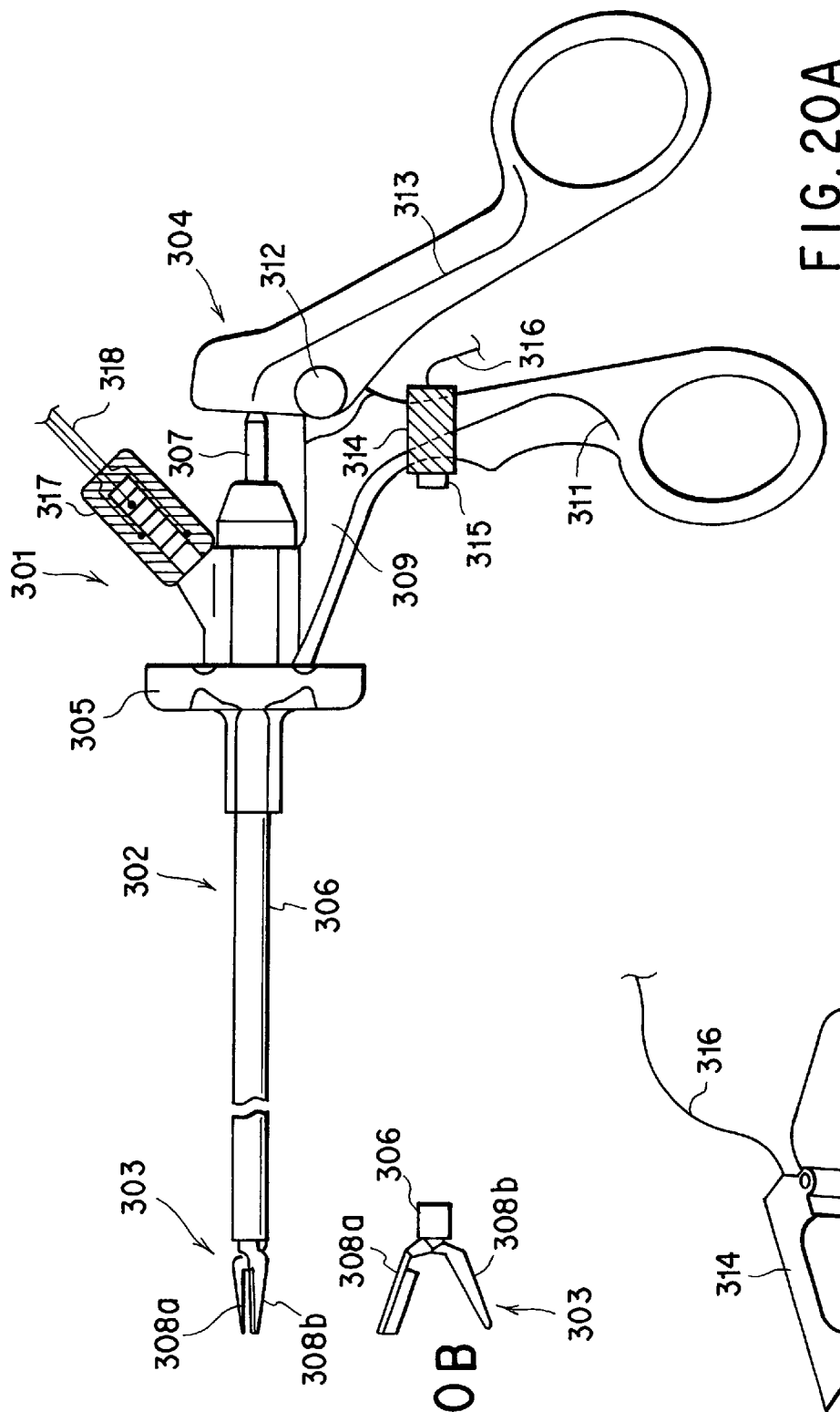
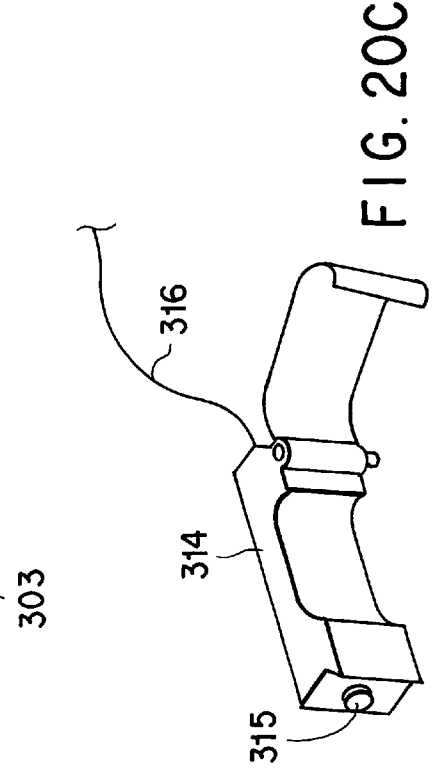

HIGH-FREQUENCY TREATMENT APPARATUS HAVING CONTROL MECHANISM FOR INCISING TISSUE AFTER COMPLETION OF COAGULATION BY HIGH-FREQUENCY TREATMENT TOOL

BACKGROUND OF THE INVENTION

The present invention relates to a high-frequency treatment apparatus which can be inserted into a vital body cavity to coagulate/incise tissue.

Generally, bipolar forceps having jaws as a pair of grasping members for grasping vital tissue and high-frequency current supply electrodes formed on the jaws are known. In use of this bipolar forceps, vital tissue to be treated is grasped between the pair of jaws, and a high-frequency current is flowed across the electrodes of the jaws, thereby coagulating the vital tissue between the jaws.

Bipolar forceps of this type are normally used for various purposes, e.g., to stop bleeding from blood vessels in vital tissue, cauterize a morbid portion or bleeding point on the surface of vital tissue, or close a uterine tube for contraception. The bipolar forceps are used for vascular hemostasis or tubal ligation; they coagulate vital tissue of a patient to be treated and also incise the coagulated vital tissue.

Conventionally, as high-frequency treatment tools of this type, a tool having projections formed on jaws so as to coagulate/incise tissue upon manipulating a manipulation portion, as disclosed in, e.g., Japanese Patent Application No. 10-11199, a tool having two insulated electrodes on the outer surfaces of a surgical scissors comprising a pair of shearing members so as to coagulate/incise tissue, as disclosed in Jpn. Pat. Appln. KOKAI Publication No. 9-173347, and a tool having two opposing coagulation electrodes and a slidable incision electrode at the center so as to incise tissue using one of the coagulation electrodes and the incision electrode, as disclosed in DE 4138116 A1 are known.

DE 4032471 C2 (corresponding to U.S. Pat. No. 5,269,780) discloses a tool which has coagulation electrodes and incision electrode at the distal end of the insertion portion and a change-over switch provided on the manipulation portion to switch the energization state between the coagulation electrodes and between the incision electrode and coagulation electrodes, thereby coagulating/incising tissue. Arrangements in DE 4138116 A1 and U.S. Pat. No. 5,267,998 also have similar switches.

In addition, as disclosed in Jpn. Pat. Appln. KOKAI Publication No. 9-108234, a tool which coats the energization portions of jaws with an insulating material to increase the current density and increase the coagulation speed is also known.

Furthermore, a bipolar coagulation/incision treatment tool disclosed in U.S. Pat. No. 2,031,682 which coagulates tissue using a coagulation electrode and then incises the tissue using an incision electrode, or a tool disclosed in U.S. Pat. No. 4,655,216 which coagulates tissue using a coagulation electrode and then cuts the tissue with scissors-shaped blades is also known.

However, the tool disclosed in Japanese Patent Application No. 10-11199 cannot sufficiently coagulate tissue in some cases because the tissue is coagulated/incised using only an incision output. Additionally, the tool disclosed in Jpn. Pat. Appln. KOKAI Publication No. 9-173347 is a surgical scissors that can incise tissue in accordance with manipulation of the physician even without coagulation, and therefore, bleeding may occur.

As the tool disclosed in DE 4138116 A1 has no jaws for grasping tissue, it cannot sufficiently close and coagulate a blood vessel. In the tool disclosed in DE 4032471 C2, if the physician incises tissue by switching the change-over switch of the manipulation portion between coagulation and incision before the tissue completely coagulates, bleeding may occur. The change-over switch merely switches the energization state. To switch between the coagulation output and the incision output, for example, a foot switch must be operated with a foot simultaneously with the operation of the change-over switch. For this reason, the operation not only is cumbersome but also cannot continuously and smoothly switch from coagulation to incision.

For the tool disclosed in Jpn. Pat. Appln. KOKAI Publication No. 9-108234, the jaws must be coated with an electrical insulating material.

For the tool disclosed in U.S. Pat. No. 2,031,682, after coagulation, the user must operate an incision means different from the coagulation means. This makes the operability poor and also poses a problem of interruption of operation. In addition, the scissors-like blades of the tool disclosed in U.S. Pat. No. 4,655,216 are poor in durability and become blunt after repeated use.

BRIEF SUMMARY OF THE INVENTION

It is therefore an object of the present invention to provide a high-frequency treatment apparatus capable of properly coagulating tissue and easily and smoothly performing coagulation/incision or switching operation to incision.

In order to achieve the above object, according to the first aspect of the present invention, there is provided a high-frequency treatment apparatus comprising a high-frequency treatment tool having, at a distal end portion, a treatment portion for coagulating or incising tissue, a manipulation portion, and a high-frequency output power supply unit electrically connected to the high-frequency treatment tool to selectively generate a high-frequency coagulation output for coagulating tissue and a high-frequency incision output for incising the tissue on the basis of a signal generated upon manipulating the manipulation portion, wherein the manipulation portion has a control mechanism for causing the high-frequency treatment tool to incise the tissue after coagulation of the tissue by the high-frequency treatment tool is completed.

According to the second aspect of the present invention, in the high-frequency treatment apparatus of the first aspect, the high-frequency output power supply unit has a control section for controlling to generate the high-frequency coagulation output at a first manipulation position of the manipulation portion and the high-frequency incision output at a second manipulation position of the manipulation portion.

According to the third aspect of the present invention, there is provided a high-frequency treatment apparatus comprising a coagulation/incision treatment tool, the coagulation/incision treatment tool comprising a treatment portion including at least three electrodes insulated from each other, a handle portion having a movable handle for opening/closing the treatment portion, and a selection member for selecting at least two of the three electrodes and connecting the two electrodes to a high-frequency power supply in a first state of the movable handle, and selecting a combination of at least two electrodes, which is different from that in the first state, and connecting the two electrodes to the high-frequency power supply in a second state of the movable handle, wherein in the first state, the movable handle moves from a substantially fully open position to a predetermined position between the substantially fully open position and a fully closed position, in the second state, the movable handle moves from the predetermined position to a substantially fully closed position, and the selection member is actuated in accordance with the position of the movable handle.

According to the fourth aspect of the present invention, there is provided a high-frequency treatment apparatus having a coagulation/incision treatment tool, the coagulation/incision treatment tool comprising a treatment portion including at least three electrodes insulated from each other, a handle portion for opening/closing the treatment portion, three electrical input portions formed in the handle portion in correspondence with the three electrodes, and a selection member for causing a high-frequency power supply to energize at least two of the three electrodes in a first state and causing the high-frequency power supply to energize a combination of at least two of the three electrodes, which is different from that in the first state, in a second state.

According to the fifth aspect of the present invention, in the high-frequency treatment apparatus of the first aspect, the high-frequency treatment tool has at least one hand switch arranged at a predetermined position and capable of manual operation as the control mechanism, and the high-frequency output power supply unit has a control section for switching the output state from the high-frequency coagulation output to the high-frequency incision output on the basis of an electrical signal generated upon operating the hand switch.

According to the sixth aspect of the present invention, in the high-frequency treatment apparatus of the first aspect, the high-frequency output power supply unit comprises a control section for notifying a user that tissue coagulation has reached a predetermined coagulation state and switching operation from coagulation to incision at a switching point determined by the user on the basis of the notification.

According to the seventh aspect of the present invention, in the high-frequency treatment apparatus of the first aspect, the high-frequency output power supply unit further comprises a control section having, as a series of coagulation/incision operations of the high-frequency treatment tool, at least two modes of an automatic cut mode in which completion of coagulation is determined after generation of the coagulation output to automatically switch the coagulation output to the incision output, a semiautomatic cut mode in which a user determines a switching point from the coagulation output to the incision output on the basis of a notified coagulation state, and a manual mode in which the coagulation output and the incision output are independently manually generated, and a mode switching section capable of switching the modes.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 4A, 4B, and 4C are graphs showing the second embodiment of the present invention in which FIGS. 4A and 4B show the relationship between the output and impedance, and FIG. 4C shows a change in impedance upon coagulation;

FIGS. 7A, 7B, and 7C are explanatory views of the function of the fourth embodiment of the present invention;

FIG. 8 is a longitudinal sectional view showing a treatment portion of the fourth embodiment;

FIG. 9 is a longitudinal sectional view showing a manipulation portion of the fourth embodiment;

FIG. 10 is a longitudinal sectional view showing the fifth embodiment of the present invention in which tissue is coagulated by a bipolar coagulation/incision treatment tool;

FIG. 11 is a longitudinal sectional view showing a state wherein tissue is incised in the fifth embodiment;

FIGS. 20A, 20B, and 20C are views showing the overall arrangement of a tripolar high-frequency treatment tool to which the 11th embodiment of the present invention is applied;

DETAILED DESCRIPTION OF THE INVENTION

The embodiments of the present invention will be described below with reference to the accompanying drawing.

(First Embodiment)

Figure 1:
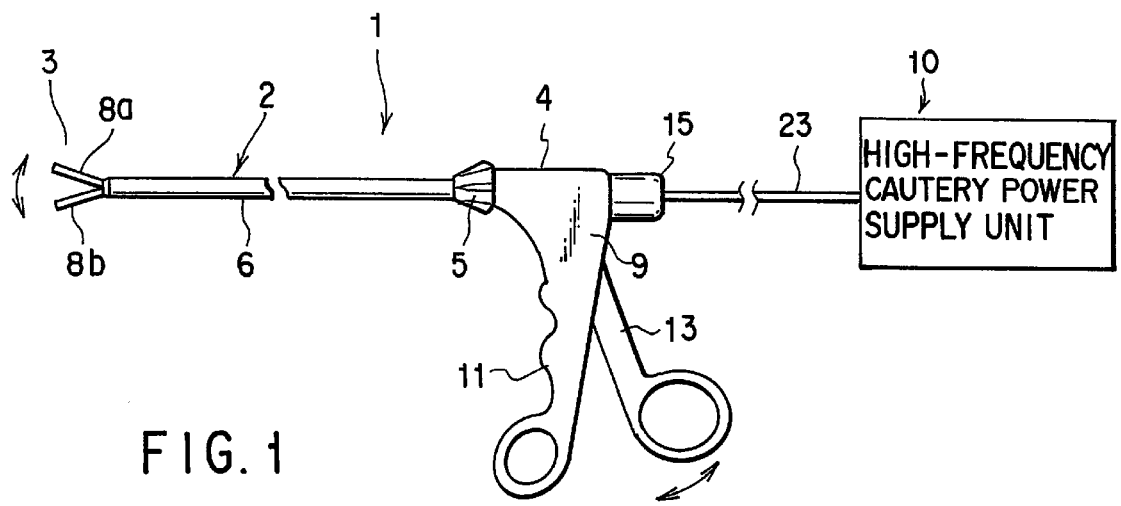
FIG. 1 is a side view showing the overall arrangement of a high-frequency treatment apparatus according to the first embodiment of the present invention.
Figure 2:
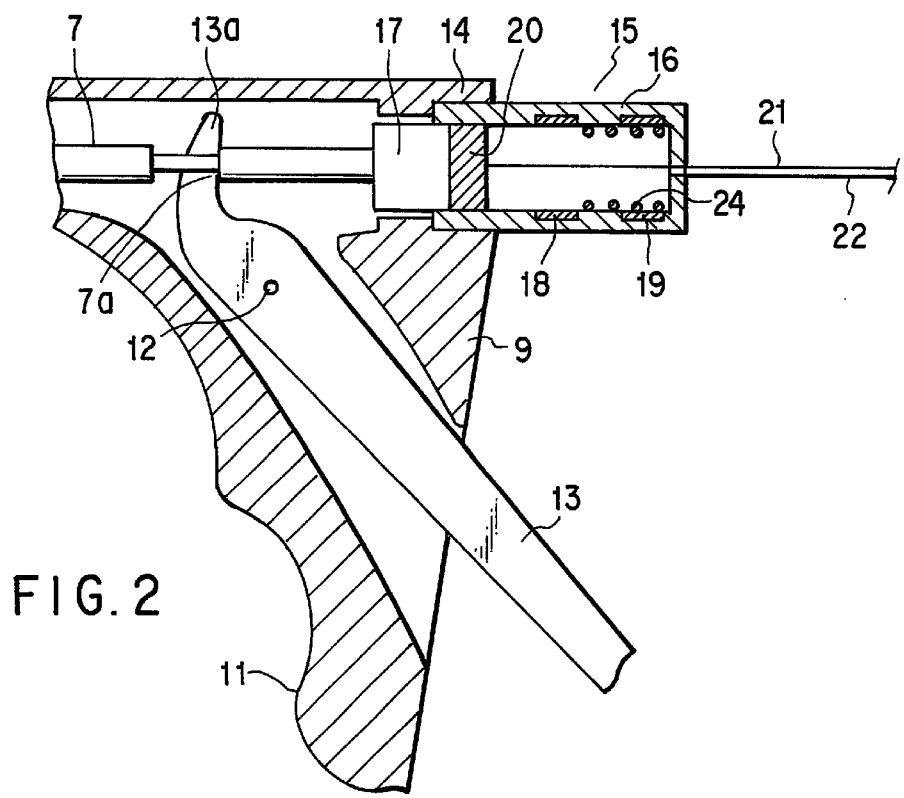
FIG. 2 is a longitudinal sectional view of a manipulation portion of the first embodiment.

FIGS. 1 to 3C show the first embodiment. FIG. 1 is a side view showing the overall arrangement of a high-frequency treatment apparatus. As shown in FIGS. 1 and 2, the high-frequency treatment apparatus comprises bipolar forceps 1 as a high-frequency treatment tool and a high-frequency cautery power supply unit (high-frequency output power supply unit) 10. The bipolar forceps 1 have a long insertion portion 2 to be inserted into a body cavity of a patient, a treatment portion 3 located at the distal end portion of the insertion portion 2 to grasp and coagulate/incise vital tissue in the body cavity and capable of being energized, and a manipulation portion 4 coupled to the proximal end portion of the insertion portion 2.

The insertion portion 2 has a sheath 6 rotatably supported by a rotary manipulation portion 5 of the manipulation portion 4. A driving shaft 7 extending into the manipulation portion 4 is inserted into the sheath 6 to freely move back and forth. A pair of jaws 8a and 8b formed from electrodes for constructing the treatment portion 3 are fixed at the distal end portion of the driving shaft 7 while being biased in a direction to open.

The manipulation portion 4 has a fixed handle 11 formed integrally with a manipulation portion main body 9 and a movable handle 13 attached to the manipulation portion main body 9 to freely pivot about a pivot pin 12. A lock 13a is formed at an end portion on the opposite side of the finger hook of the movable handle 13 and locked by a step 7a formed at the proximal end portion of the driving shaft 7. When the driving shaft 7 is moved back and forth by pivoting the movable handle 13, the jaws 8a and 8b open/close.

The manipulation portion main body 9 has an opening 14 at a portion located on the extended line of the distal end portion of the driving shaft 7, and an output switching mechanism 15 as a control mechanism is fitted in the opening 14. This output switching mechanism 15 has a cylindrical member 16 formed from an electrical insulating material such as a synthetic resin and fixed at the opening 14, a sliding member 17 formed from an electrical insulating material such as a synthetic resin and movable back and forth in the cylindrical member 16 in the axial direction, and the like.

A ring-shaped first contact 18 on the coagulation current output side is formed in the middle portion in the axial direction on the inner surface of the cylindrical member 16, and a ring-shaped second contact 19 on the incision current output side is formed at the proximal end portion on the inner surface of the cylindrical member 16. A ring-shaped sliding contact 20 is formed on the outer surface of the sliding member 17 to selectively come into contact with the first contact 18 or second contact 19.

An output line 21 is connected to the sliding contact 20. A detection signal line 22 is connected to the first and second contacts 18 and 19. The two lines 21 and 22 are connected to the high-frequency cautery power supply unit 10 through an electrical cord 23 extending from the manipulation portion 4. The cylindrical member 16 incorporates a coil spring 24. The coil spring 24 has a length about ½ the axial length of the cylindrical member 16 and provided on the proximal end side of the cylindrical member 16. The sliding member 17 does not receive the reaction force of the coil spring 24 until the sliding member 17 moves back to bring the sliding contact 20 into contact with the first contact 18. After the sliding member 17 comes into contact with the coil spring 24 and until the sliding member 17 further moves back to bring the sliding contact 20 into contact with the second contact 19, the sliding member 17 receives the reaction force of the coil spring 24 and therefore moves back against the spring force of the coil spring 24.

The function of the first embodiment will be described next.

The electrical cord 23 of the bipolar forceps 1 is electrically connected to the high-frequency cautery power supply unit 10. The insertion portion 2 of the bipolar forceps 1 is inserted into a body cavity of a patient, and the treatment portion 3 at the distal end of the insertion portion 2 is moved to a position near vital tissue to be treated in the body. Initially, the movable handle 13 of the manipulation portion 4 is separated from the fixed handle 11, the driving shaft 7 is set forth to open the jaws 8a and 8b projecting from the sheath 6, and the sliding contact 20 is in contact with neither of the first and second contacts 18 and 19.

Figure 3A:
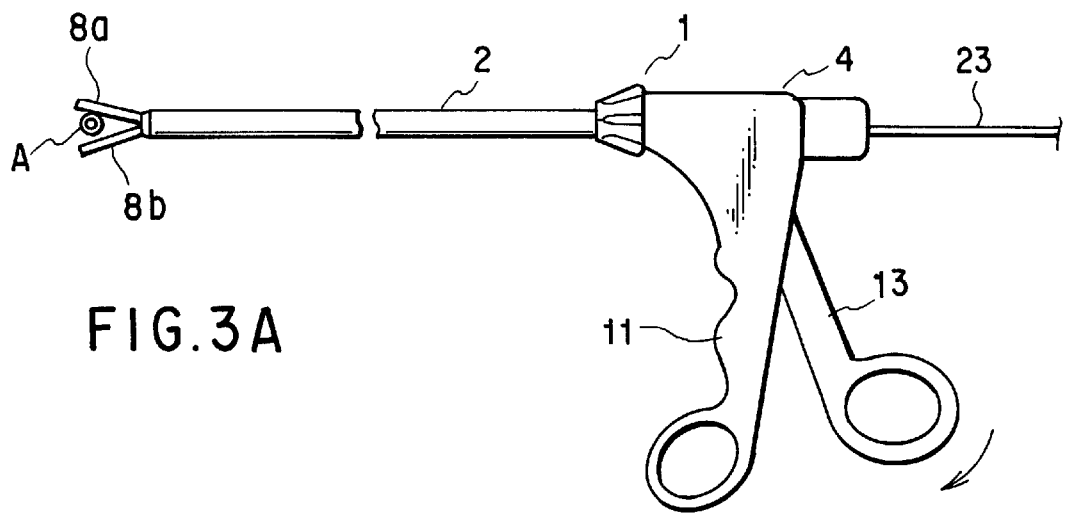
FIGS. 3A, 3B, and 3C are explanatory views of the function of the first embodiment.
Figure 3B:
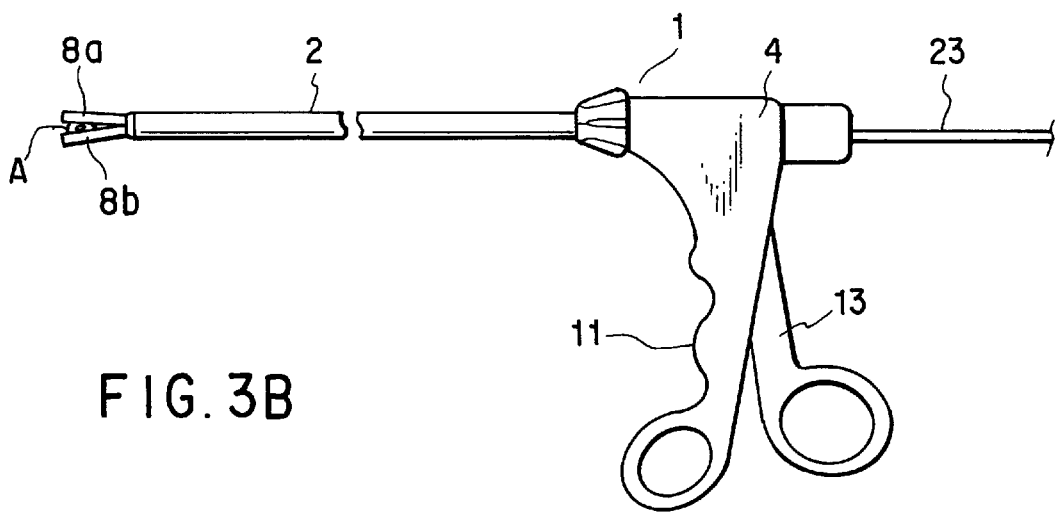
Figure 3C:
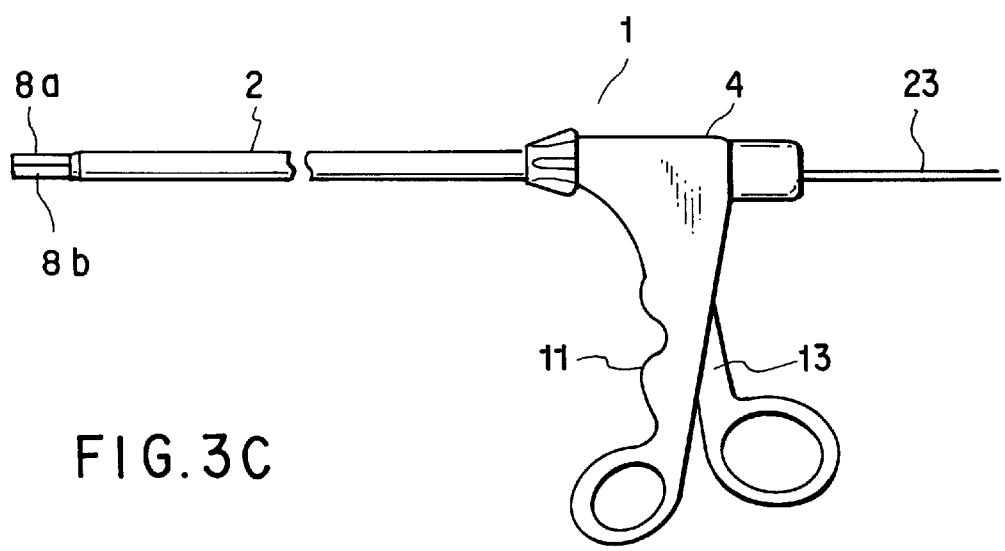

As shown in FIG. 3A, vital tissue A to be treated is sandwiched between the opened jaws 8a and 8b. When the movable handle 13 is pivoted to the fixed handle 11 side, the lock 13a is locked by the step 7a of the driving shaft 7, and the driving shaft 7 moves back. As the driving shaft 7 moves back, the jaws 8a and 8b retreat into the sheath 6 and close, as shown in FIG. 3B, so the vital tissue A is grasped by the pair of jaws 8a and 8b.

Since the sliding member 17 slidably moves back to the rear side of the cylindrical member 16 in accordance with retreat of the driving shaft 7, the sliding contact 20 comes into contact with the first contact 18, and the output line 21 and detection signal line 22 make a circuit. A high-frequency current flows from the high-frequency cautery power supply unit 10 through the electrical cord 23. A coagulation current flows across the jaws 8a and 8b to coagulate the vital tissue A.

When the movable handle 13 is further pivoted to the fixed handle 11 side, the jaws 8a and 8b further close, and the sliding member 17 further moves back and comes into contact with the distal end portion of the coil spring 24. The movable handle 13 receives the reaction force of the coil spring 24. The reaction force is transmitted to the hand or fingers of the physician who is pivotally manipulating the movable handle 13, so he/she can sense that the sliding member 17 has touched the coil spring 24.

When the sliding member 17 further moves back against the biasing force of the coil spring 24 in accordance with pivotal movement of the movable handle 13, the sliding contact 20 leaves the first contact 18, and the coagulation current temporarily stops. After this, the sliding contact 20 comes into contact with the second contact 19, and the output line 21 and detection signal line 22 make a circuit. A high-frequency current flows from the high-frequency cautery power supply unit 10 through the electrical cord 23. An incision current flows across the jaws 8*a* and 8*b* to incise the vital tissue A.

In this way, the vital tissue A is coagulated, and the coagulated portion is incised by a series of pivot operations of the movable handle 13. When the sliding member 17 moving back in accordance with pivotal movement of the movable handle 13 abuts against the coil spring 24 and receives the reaction force of the coil spring 24, the reaction force is transmitted to the hand or fingers of the physician to prevent him/her from pivoting the movable handle 13 at a stroke. The physician can feel the shift from coagulation to incision and always start incision after tissue is completely coagulated.

According to the above-described embodiment, incision can be started after the vital tissue A is completely coagulated. In addition, since the coagulation current and incision current are automatically switched, no switching operation is required, and the operability can be improved.

(Second Embodiment)

In a series of coagulation/incision operations, a high-frequency cautery power supply unit may automatically determine completion of coagulation after the start of coagulation output, stop the coagulation operation, and then automatically switch to incision output. In this method, to prevent hemorrhage, it must be accurately detected when coagulation is sufficiently done. In the second embodiment, completion of coagulation is detected by detecting a change in impedance. The method of this embodiment is also used in the 11th and 12th embodiments to be described later.

Figure 4A:
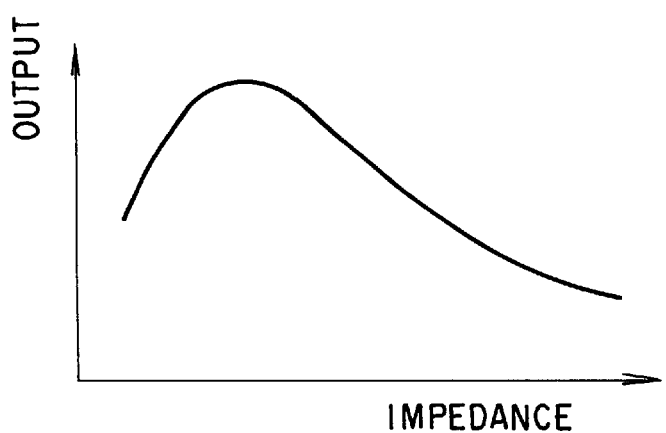
Figure 4B:
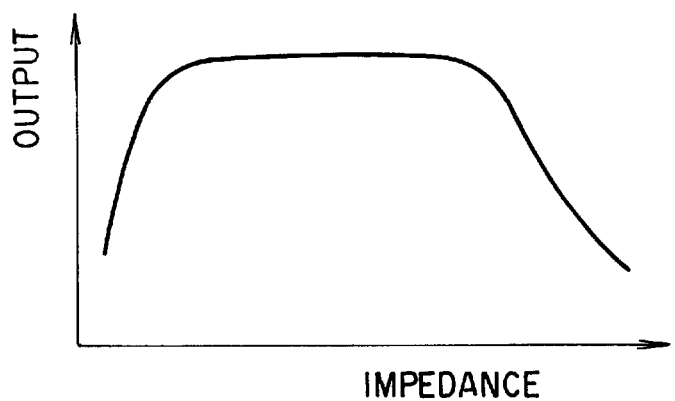
Figure 4C:
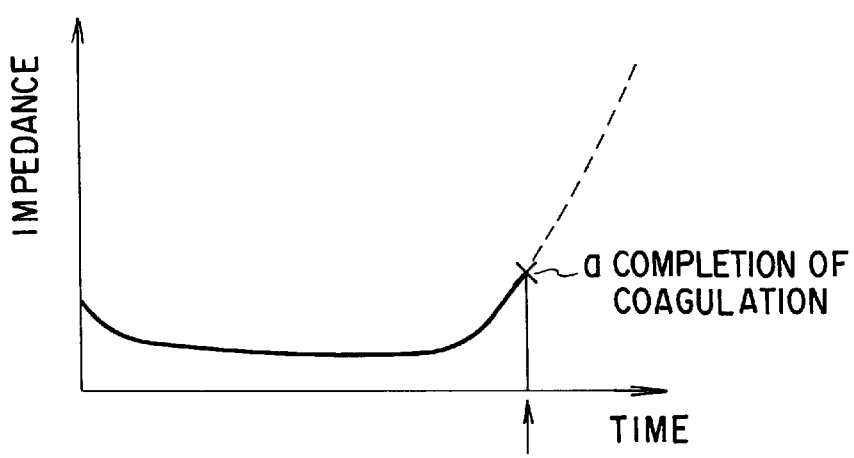

FIGS. 4A, 4B, and 4C are views for explaining the method of detecting the point of complete coagulation on the basis of a change in impedance. More specifically, a coagulation current is output in a mode with load characteristics in which the output decreases with increasing impedance upon coagulation, as shown in FIG. 4A. However, an incision current is output in a constant power output mode in which the output does not decrease even when the impedance increases, as shown in FIG. 4B. As shown in FIG. 4C, in impedance control, the power supply unit determines completion of coagulation at a point a where the impedance which has temporarily decreased in accordance with the elapse of coagulation time increases again. With this arrangement, vital tissue A can be incised by flowing an incision current after coagulation is properly completed. That is, the coagulation current and incision current can be automatically switched.

(Third Embodiment)

Figure 5:
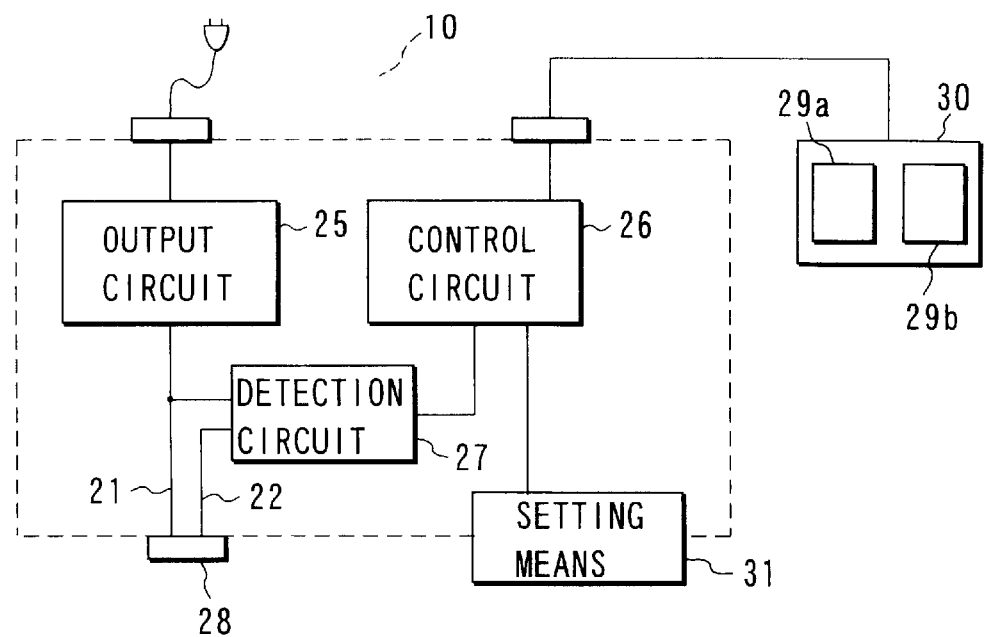
FIG. 5 is a block diagram of a high-frequency cautery power supply unit according to the third embodiment of the present invention.
Figure 6:
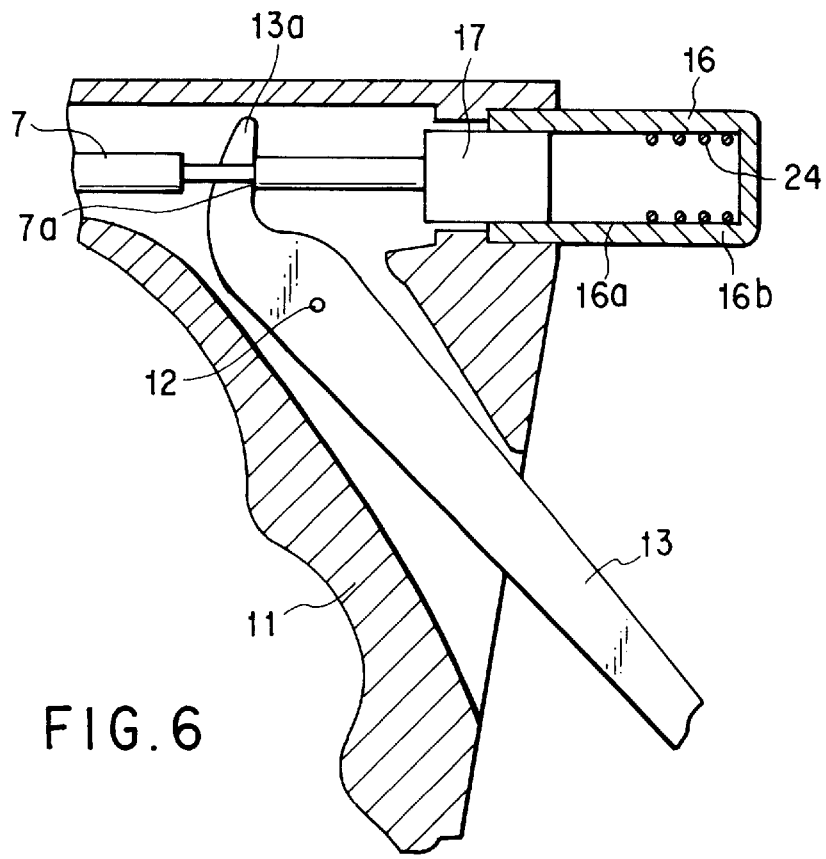
FIG. 6 is a longitudinal sectional view of a manipulation portion of the third embodiment.

FIGS. 5 and 6 show the third embodiment. FIG. 5 is a block diagram showing the internal arrangement of a high-frequency cautery power supply unit 10. FIG. 6 is a longitudinal sectional view showing the internal structure of a manipulation portion 4. As shown in FIG. 5, the high-frequency cautery power supply unit 10 incorporates a high-frequency output circuit 25, a control circuit 26, and a detection circuit 27. An output line 21 connected to an output connector 28 is connected to the output circuit 25 and detection circuit 27. A detection signal line 22 is connected to the detection circuit 27. The control circuit 26 is connected to a foot switch 30 with a coagulation switch 29*a* and an incision switch 29*b*, and has a setting means 31.

The setting means 31 has setting 1, setting 2, and setting 3. Setting 1 is the mode of the first embodiment in which a coagulation current is flowed when a first contact 18 and a sliding contact 20 sliding in accordance with pivotal movement of a movable handle 13 make a circuit, and an incision current is flowed when the sliding contact 20 and a second contact 19 make a circuit, thereby starting incision after coagulation is completed.

Setting 2 is a mode to be described later, in which the coagulation switch 29*a* of the foot switch 30 is turned on to flow a coagulation current to coagulate tissue when a sliding member 17 sliding in accordance with pivotal movement of the movable handle 13 has reached the coagulation position, and the incision switch 29*b* of the foot switch 30 is turned on to flow an incision current to incise tissue when the sliding member 17 has reached the incision position. The incision switch 29*b* is not turned on unless the coagulation switch 29*a* is turned on to flow the coagulation current. Setting 3 is a manual mode in which the coagulation and incision currents can be flowed independently of setting 1 or 2.

A supplementary explanation will be given for setting 2. As shown in FIG. 6, a cylindrical member 16 arranged in a manipulation portion main body 9 incorporates a coil spring 24. The coil spring 24 has a length about ½ the axial length of the cylindrical member 16 and provided on the proximal end side of the cylindrical member 16. The sliding member 17 does not receive the reaction force of the coil spring 24 until the sliding member 17 moves back to a coagulation position 16*a*. The sliding member 17 receives the reaction force of the coil spring 24 until the sliding member 17 further moves back to an incision position 16*b*. The sliding member 17 moves back against the spring force of the coil spring 24.

When the movable handle 13 is pivoted to a fixed handle 11 side, the driving shaft 7 moves back, and the sliding member 17 moves back in accordance with retreat of the driving shaft 7. When the physician senses, through his/her hand or fingers grasping the movable handle 13, that the sliding member 17 has reached the coagulation position 16*a*, i.e., the sliding member 17 has come into contact with the coil spring 24, the coagulation switch 29*a* of the foot switch 30 is turned on to flow a high-frequency current from the high-frequency cautery power supply unit 10 through an electrical cord 23. A coagulation current flows across jaws 8*a* and 8*b* to coagulate vital tissue A.

When the sliding member 17 further moves back against the biasing force of the coil spring 24 in accordance with pivotal movement of the movable handle 13, the sliding member 17 reaches the incision position 16*b* at the rear end of the cylindrical member 16. At this time, the incision switch 29*b* of the foot switch 30 is turned on to flow a high-frequency current from the high-frequency cautery power supply unit 10 through the electrical cord 23. An incision current flows across the jaws 8*a* and 8*b* to incise the vital tissue A.

As described above, the vital tissue A is coagulated, and the coagulated portion is incised by the series of pivot operations of the movable handle 13. When the sliding member 17 moving back in accordance with pivotal movement of the movable handle 13 abuts against the coil spring 24 and receives the reaction force of the coil spring 24, the reaction force is transmitted to the hand or fingers of the physician. Hence, the physician can actually feel the shift from coagulation to incision and appropriately operate the foot switch 30.

(Fourth Embodiment)

FIGS. 7A to 9 show the fourth embodiment. The same reference numerals as in the first embodiment denote the same parts in the fourth embodiment, and a detailed description thereof will be omitted. A sheath 6 forming an insertion portion 2 has, at its distal end portion, a first coagulation jaw 31, a second coagulation jaw 32, and an incision jaw 33.

The first and second coagulation jaws 31 and 32 having a rectangular loop shape are fixed at the distal end portion of a driving shaft 7 and biased in a direction to open. The incision jaw 33 is fixed at the distal end portion of an incision jaw driving shaft 34 which is disposed in the sheath 6 parallel to the driving shaft 7 to freely move back and forth. The incision jaw 33 has a rod shape with a triangular section and is biased to separate from the second coagulation jaw 32. The driving shaft 7 and incision jaw driving shaft 34 have insulating coats on their outer surfaces located on the sheath 6.

As shown in FIG. 9, the incision jaw driving shaft 34 extends into a manipulation portion main body 9 and has a projection 34a at its proximal end portion on the rear side of a step 7a of the driving shaft 7. A leaf spring 35 with one end fixed in the manipulation portion main body 9 is pressed against the rear end of the projection 34a to bias the incision jaw driving shaft 34 to the distal end side, i.e., in a direction in which the incision jaw 33 projects from the distal end portion of the sheath 6. An incision jaw output line 36 is connected to the incision jaw driving shaft 34.

As shown in FIG. 7A, when vital tissue to be treated is inserted between the opened first and second coagulation jaws 31 and 32, and a movable handle 13 is pivoted to the fixed handle 11 side, a lock 13a is locked by the step 7a of the driving shaft 7, and the driving shaft 7 moves back. In accordance with retreat of the driving shaft 7, the first and second coagulation jaws 31 and 32 retract into the sheath 6 and close, as shown in FIG. 7B, so the vital tissue is grasped between the first and second coagulation jaws 31 and 32.

At this time, since a sliding member 17 slidably moves back to the rear side of a cylindrical member 16 in accordance with retreat of the driving shaft 7, a sliding contact 20 comes into contact with a first contact 18, and an output line 21 and a detection signal line 22 make a circuit. A high-frequency current flows from a high-frequency cautery power supply unit 10 through an electrical cord 23. A coagulation current flows across the first and second coagulation jaws 31 and 32 to coagulate the vital tissue.

When the movable handle 13 is further pivoted to the fixed handle 11 side, the lock 13a of the movable handle 13 abuts against the projection 34a of the incision jaw driving shaft 34 to move the incision jaw driving shaft 34 back against the biasing force of the leaf spring 35, and the incision jaw 33 retracts into the sheath 6. Hence, as shown in FIG. 7C, the incision jaw 33 pivots to the first coagulation jaw 31 side and close. Simultaneously, the sliding member 17 further moves back to abut against the distal end portion of a coil spring 24. The reaction force of the coil spring 24, which is received by the movable handle 13, is transmitted to the hand or fingers of the physician who is pivoting the movable handle 13, so the physician can sense that the sliding member 17 has abutted against the coil spring 24.

When the sliding member 17 further moves back against the biasing force of the coil spring 24 in accordance with pivotal movement of the movable handle 13, the sliding contact 20 leaves the first contact 18, and the coagulation current temporarily stops. After this, the sliding contact 20 comes into contact with a second contact 19, and the output line 21 and detection signal line 22 make a circuit. A high-frequency current flows from the high-frequency cautery power supply unit 10 through the electrical cord 23. An incision current flows across the incision jaw 33 and first coagulation jaw 31 to incise the vital tissue.

Hence, the vital tissue can be incised after it is completely coagulated. In addition, since the coagulation current and incision current are automatically switched, the operability can be improved.

(Fifth Embodiment)

Figure 12:
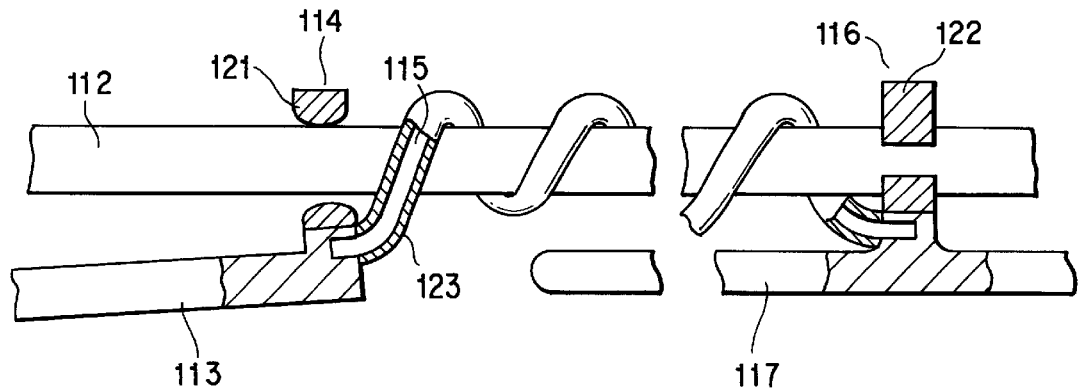
FIG. 12 is a partially cutaway enlarged side view of a driving shaft connection portion of the fifth embodiment.

FIGS. 10 to 12 show the fifth embodiment. FIG. 10 is a longitudinal sectional view showing tissue coagulation by a bipolar coagulation/incision treatment tool. FIG. 11 is a longitudinal sectional view showing tissue incision. FIG. 12 is a partially cutaway enlarged side view of a driving shaft connection portion.

A bipolar coagulation/incision treatment tool 101 comprises a treatment portion 102, an insertion portion 103, and a handle portion 104. The treatment portion 102 has a fixed coagulation jaw 105, a movable coagulation jaw 106, and an incision jaw 107 hidden in a groove 106a of the movable coagulation jaw 106. The handle portion 104 has a movable handle 108 and a fixed handle 109. The treatment portion 102 and handle portion 104 are connected through the insertion portion 103. The insertion portion 103 has an insertion pipe 111 covered with an insulating tube 110.

The incision jaw 107 is connected to the movable handle 108 through a driving shaft 112. A driving shaft 113 is connected to the movable coagulation jaw 106. The driving shaft 113 has a coil spring 115 and a guide 114 slidable with respect to the driving shaft 112. One end of the spring 115 is fixed to the proximal end portion of the guide 114, and the other end is connected to a fixed portion 116 fixed on the driving shaft 112. The fixed portion 116 has a biasing shaft 117 with a length larger than the natural length of the spring 115 in a far-end direction. The biasing shaft 117 abuts against the guide 114 to always apply a tensile force, i.e., an initial biasing force to the spring 115. Unless a force larger than the initial biasing force is applied to the driving shaft 113, the driving shafts 112 and 113 integrally move back and forth to open/close the movable coagulation jaw 106 and incision jaw 107. An energization shaft 118 extending to the handle portion 104 side is arranged on the near-end side of the fixed portion 116.

The three jaws, i.e., the fixed coagulation jaw 105, movable coagulation jaw 106, and incision jaw 107 are insulated from each other by an insulating means (not shown). The jaws 105, 106, and 107 can be energized from a high-frequency power supply by a plug 119 attached to the handle portion 104 through a cable 120.

Referring to FIG. 12, the guide 114 and fixed portion 116 are electrically connected through the spring 115, whereby the driving shaft 113 and energization shaft 118 are electrically connected. The guide 114 and fixed portion 116 respectively have insulating members 121 and 122 made of, e.g., a resin at those portions which are in contact with the driving shaft 112. The spring 115 is covered with an insulating tube 123. The driving shaft 112 is also covered with an insulating tube (not shown). Hence, the incision jaw 107 is energized through the driving shaft 112. The movable coagulation jaw 106 is energized through the driving shaft 113, spring 115, and energization shaft 118. The fixed coagulation jaw 105 is energized through the insertion pipe 111 of the insertion portion 103. The driving shafts 112 and 113 and insertion pipe 111 are insulated from each other in the handle portion 104 and connected to the plug 119.

In this embodiment, the movable coagulation jaw 106 opens/closes with respect to the fixed coagulation jaw 105. However, two movable coagulation jaws and one incision jaw may be used, as is generally known, without posing any problem.

The function of the fifth embodiment will be described next. As shown in FIG. 10, the movable handle 108 is manipulated to close the movable coagulation jaw 106, and a coagulation current is flowed across the movable coagulation jaw 106 and fixed coagulation jaw 105 to coagulate tissue. When coagulation is complete, the movable handle 108 is closed in a direction indicated by an arrow, as indicated by an alternate long and two-dashed line in FIG. 11, and an incision current is flowed across the incision jaw 107 and fixed coagulation jaw 105 to incise the tissue.

As shown in FIG. 11, when the movable handle 108 is further closed from the state shown in FIG. 10, the driving shaft 113 moves to the near-end side together with the driving shaft 112 as the tissue deforms because it is seized between the fixed coagulation jaw 105 and movable coagulation jaw 106. When a force larger than the initial biasing force of the spring 115 is applied to the driving shaft 113, only the driving shaft 112 moves back while deforming the spring 115. The incision jaw 107 projects from the movable coagulation jaw 106 and incises the tissue by synergy with the incision current. To manipulate the incision jaw 107, the movable handle 108 is closed against the deformation of the spring 115. For this reason, the user can detect manipulation of the incision jaw 107 on the basis of a clear change in force.

According to the fifth embodiment, after the movable handle is closed midway to coagulate tissue, the tissue can be continuously incised without switching the operation, resulting a good operability. In addition, since the incision jaw is closed after the coagulation jaw is closed, a completely coagulated portion can be incised, and the tissue can be prevented from being stretched by the incision jaw or escaping.

(Sixth Embodiment)

Figure 13:
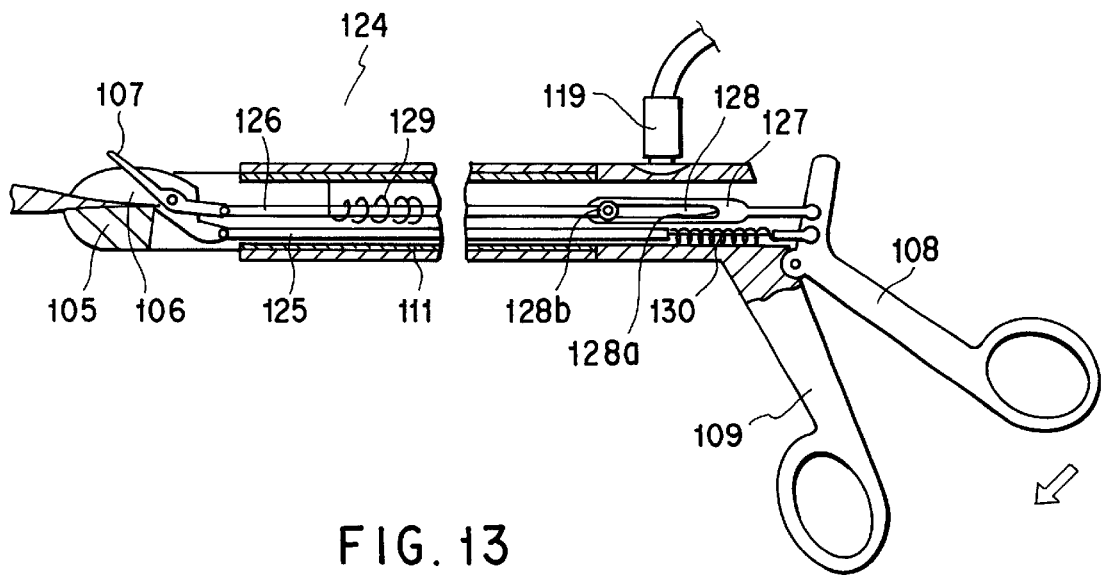
FIG. 13 is a longitudinal sectional view showing the sixth embodiment of the present invention in which only coagulation jaws are closed.

FIG. 13 is a longitudinal sectional view showing the sixth embodiment in which only the coagulation jaw is closed. The same reference numerals as in the fifth embodiment denote the same parts in the sixth embodiment, and a detailed description thereof will be omitted. A bipolar coagulation/incision treatment tool 124 has a driving shaft 125 connected to a movable coagulation jaw 106 and a front driving shaft 126 connected to an incision jaw 107. The front driving shaft 126 is connected to a movable handle 108 through a rear driving shaft 127. The rear driving shaft 127 has a guide groove 128 such that the rear driving shaft 127 can slide with respect to the front driving shaft 126.

A near-end-side end portion 128a of the guide groove 128 is set to be sufficiently long so that only the rear driving shaft 127 moves back and forth while fixing the front driving shaft 126, i.e., preventing the incision jaw 107 from closing within the opening/closing range of the movable coagulation jaw 106. On the other hand, a far-end-side end portion 128b of the guide groove 128 is set at a position where the front driving shaft 126 and rear driving shaft 127 abut against each other when the movable coagulation jaw 106 is substantially closed.

The front driving shaft 126 has, on an insertion pipe 111, a spring 129 always acting to open the incision jaw 107. The driving shaft 125 also has, on its axis, a spring 130 having an initial biasing force.

The movable coagulation jaw 106 is energized through the driving shaft 125, the incision jaw 107 is energized through the front driving shaft 126 and rear driving shaft 127, and a fixed coagulation jaw 105 is energized through the insertion pipe 111. The front driving shaft 126, rear driving shaft 127, and insertion pipe 111 are energized from a high-frequency power supply through a plug 119 of a handle portion 104. The movable coagulation jaw 106, fixed coagulation jaw 105, incision jaw 107, and current paths thereto are insulated from each other.

The function of the sixth embodiment will be described next. When the movable handle 108 is closed, the driving shaft 125 and rear driving shaft 127 move to the near-end side. Tissue is grasped between the fixed coagulation jaw 105 and movable coagulation jaw 106, and a coagulation current is supplied to coagulate the tissue. At this time, the far-end-side end portion 128b of the guide groove 128 of the rear driving shaft 127 does not abut against the front driving shaft 126, and the incision jaw 107 is still open. After coagulation is completed, the movable handle 108 is further closed in a direction indicated by an arrow. The far-end-side end portion 128b of the guide groove 128 abuts against the front driving shaft 126, and the front driving shaft 126 moves to the near-end side to close the incision jaw 107. When the incision jaw 107 is closed, an incision current is flowed to incise the tissue. At this time, when a force larger than the initial biasing force of the spring 130 is applied to the driving shaft 125, the spring 130 of the driving shaft 125 deforms to prevent the movable coagulation jaw 106 from further closing. When incision is complete, the movable handle 108 is returned to the home position. The front driving shaft 126 is returned back by the spring 129 to open the incision jaw 107. The driving shaft 125 also moves to the far-end side to open the movable coagulation jaw 106. The position at which the incision jaw 107 starts to close depends on the position of the guide groove 128, and therefore, does not change. The position at which the incision jaw 107 starts to close may be indicated on the movable handle 108. According to the sixth embodiment, the incision jaw 107 always starts to close at a predetermined position, and the user can easily see it.

According to the above-described fifth and sixth embodiments, the following effects can be obtained.

(Seventh Embodiment)

Figure 14:
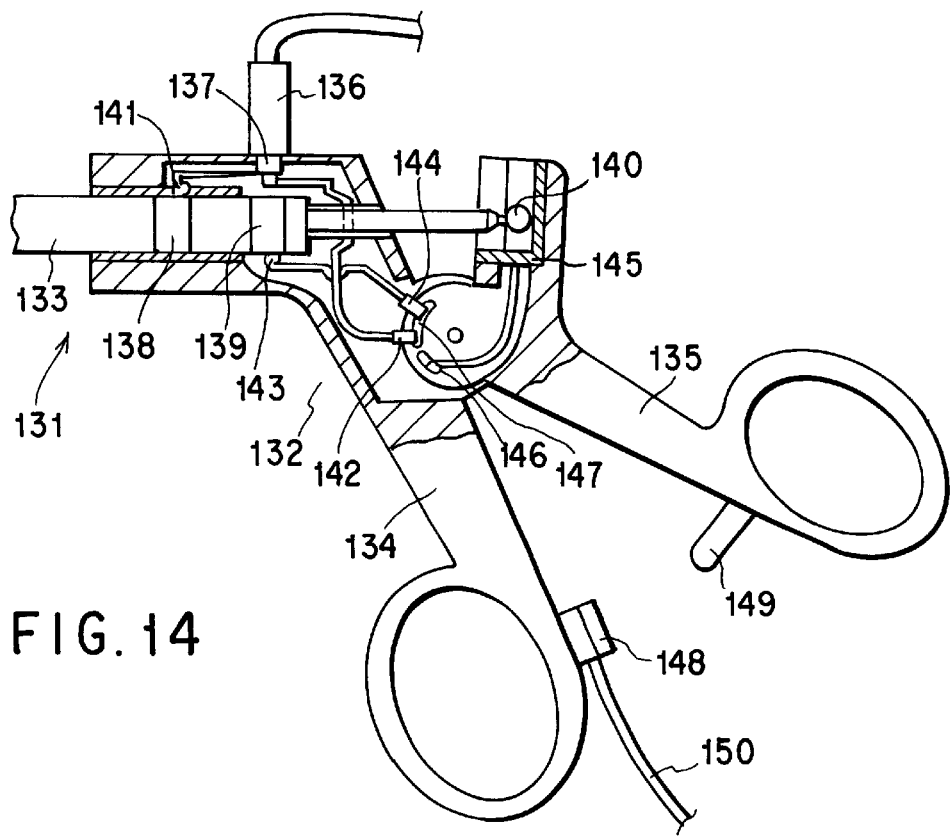
FIG. 14 is a longitudinal sectional view showing a bipolar coagulation/incision treatment tool according to the seventh embodiment of the present invention in which the current path is connected to the coagulation side.
Figure 15:
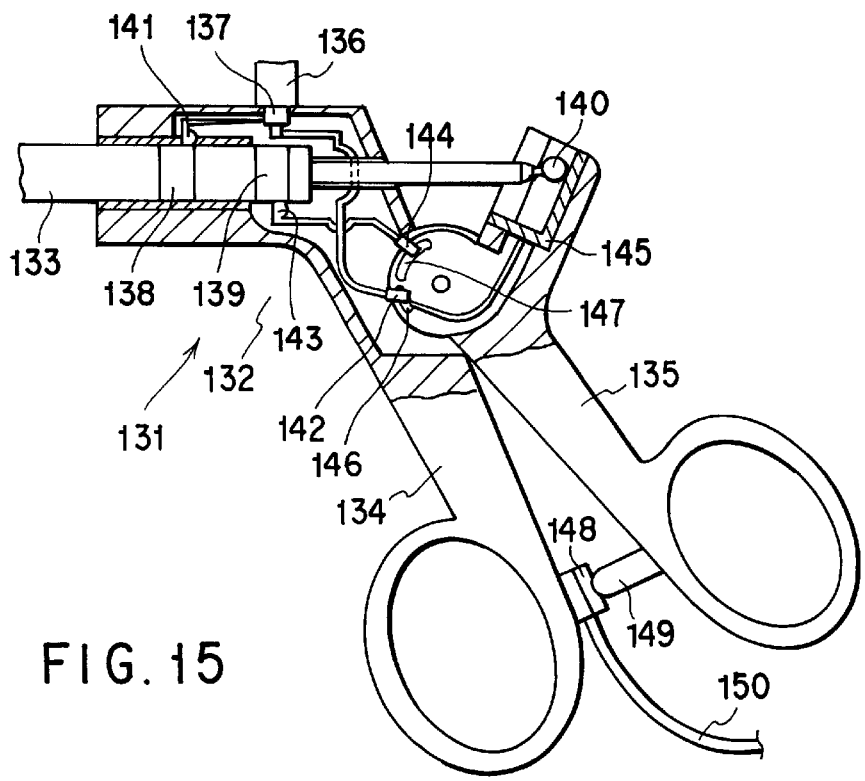
FIG. 15 is a longitudinal sectional view showing the bipolar coagulation/incision treatment tool according to the seventh embodiment of the present invention in which the current path is connected to the incision side.

FIGS. 14 and 15 show the seventh embodiment. FIG. 14 is a longitudinal sectional view showing a bipolar coagulation/incision treatment tool whose current path is connected to the coagulation side. FIG. 15 is a longitudinal sectional view showing a bipolar coagulation/incision treatment tool whose current path is connected to the incision side.

Referring to FIG. 14, a bipolar coagulation/incision treatment tool 131 comprises a handle portion 132, an insertion portion 133, and a treatment portion (not shown). The treatment portion has a tripolar structure in which a coagulation portion having two coagulation electrodes insulated from each other and an incision portion having an incision electrode insulated from the coagulation electrodes are formed. The handle portion 132 has axially supported fixed handle 134 and movable handle 135. The fixed handle 134 has a plug 137 connected to a cable 136 connected to a bipolar output (i.e., two poles) of a high-frequency power supply (not shown).

The insertion portion 133 has, on its near-end side, connection electrodes 138 and 139 for supplying a high-frequency current to the coagulation electrodes of the treatment portion and a connection electrode 140 for supplying a high-frequency current to the incision electrode of the treatment portion. One pole of the plug 137 is connected to a reception electrode 141 for receiving the connection electrode 138, and the other pole is connected to an electrical contact 142 fixed in the fixed handle 134. The connection electrode 139 is connected to an electrical contact 144 of the fixed handle 134 through a reception electrode 143.

The connection electrode 140 is connected to an arcuated electrical contact 146 fixed on the movable handle 135 concentrically with the fulcrum of the handle through a reception electrode 145. The movable handle 135 also has a substantially arcuated electrical contact 147 insulated from the electrical contact 146. These electrical contacts and reception electrodes can be formed in the handles by, e.g., insert molding.

The fixed handle 134 has a switch 148 for selecting the type of current waveform from the high-frequency power supply. The movable handle 135 has a press rod 149 for pressing the switch 148 when the movable handle 135 is closed.

The switch 148 is connected to the high-frequency power supply through a cable 150. When the switch 148 is ON, a coagulation current is selected by a current selection circuit (not shown) incorporated in the high-frequency power supply. Instead of using the switch 148, the user may arbitrarily select the current type with a foot switch or a hand switch.

The connection electrode 140 also serves as a driving shaft for opening/closing the coagulation and incision portions of the treatment portion. The insertion portion 133 can be detached from the handle portion 132. Although the cables 136 and 150 are shown as independent structures, they may be integrated into a coaxial cable.

The function of the seventh embodiment will be described next. In FIG. 14, the coagulation portion (not shown) is closed. At this time, the electrical contacts 142 and 144 engage through the electrical contact 147. Hence, the two coagulation electrodes and two poles of the plug 137 (i.e., high-frequency power supply) are connected to supply a current to the two coagulation electrodes. Next, when the movable handle 135 is further closed to actuate the incision electrode, as shown in FIG. 15, the electrical contacts 144 and 142 engage with the electrical contacts 147 and 146, respectively, to connect the two poles of the plug 137 to one of the coagulation electrodes and the incision electrode. That is, when coagulation is complete, and the movable handle 135 is further closed to actuate the incision electrode, the electrical contacts automatically switch to supply a current across the coagulation electrode and incision electrode. The handle portion 132 may have, on its exterior, marks indicating engaging electrical contacts corresponding to the open and closed positions of the movable handle 135. When the movable handle 135 is in the state shown in FIG. 15, the switch 148 is pressed and turned on. In the ON state, the high-frequency power supply selects an incision current. The switch 148 may generate a control signal for controlling the high-frequency power supply.

According to the seventh embodiment, when the movable handle is closed to actuate the incision electrode, the current path automatically switches to the incision electrode, i.e., the bipolar output (two poles) automatically switches to a tripolar output, resulting in good operability. As the bipolar output, not only a dedicated power supply but also a general electric knife power supply can be used. In addition, since the electrode engaging state is indicated on the exterior of the handle, the user can easily understand the engaging state.

(Eighth Embodiment)

Figure 16:
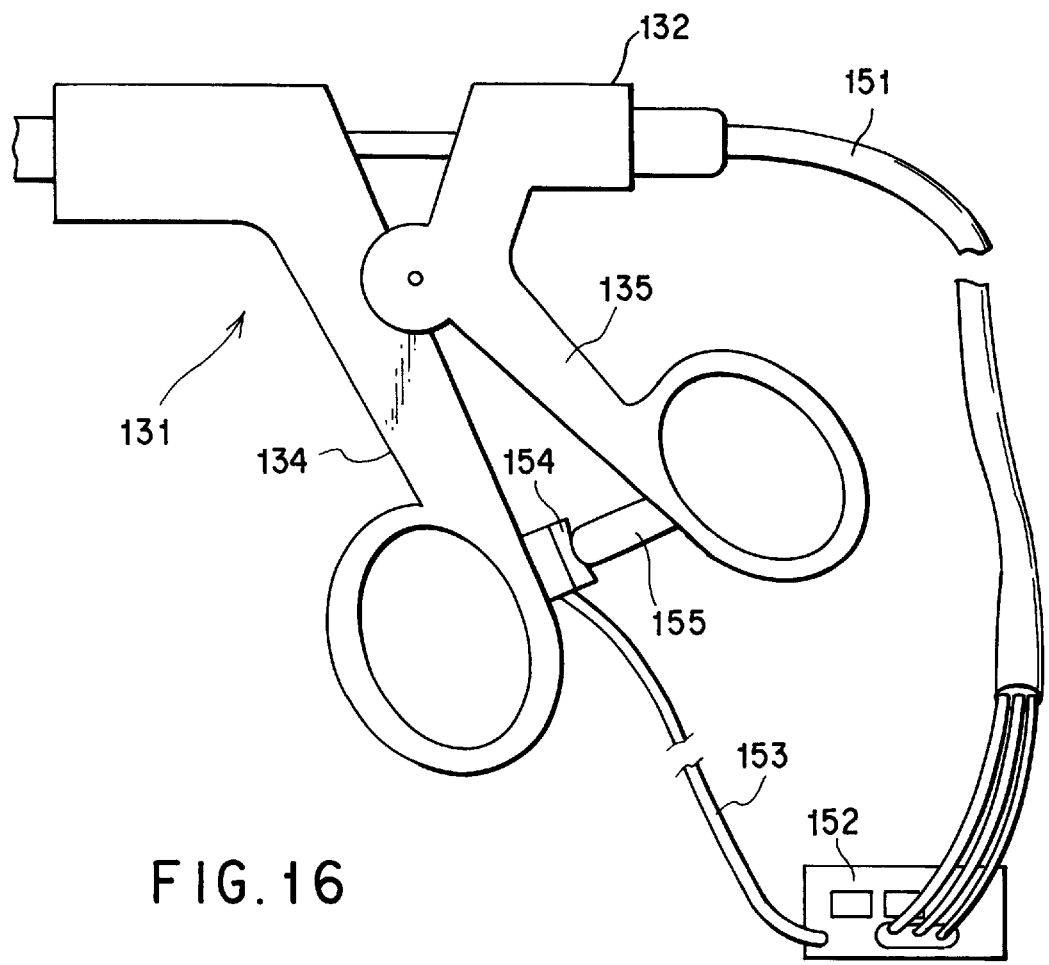
FIG. 16 is a side view showing the eighth embodiment of the present invention in which the current path is connected to the incision side.

FIG. 16 shows the eighth embodiment. The same reference numerals as in the seventh embodiment denote the same parts in the eighth embodiment, and a detailed description thereof will be omitted. FIG. 16 is a side view showing an current path connected to the incision side. This embodiment corresponds to a high-frequency power supply having a tripolar high-frequency output.

The treatment portion of a bipolar coagulation/incision treatment tool 131 has two coagulation electrodes and one incision electrode, which are connected to a high-frequency power supply 152 through a cable 151. In addition, to select two of the three poles of the high-frequency power supply 152 for energization when a movable handle 135 is closed, a press rod 155 and a switch 154 connected to the high-frequency power supply 152 through a cable 153 are used. The current type may be changed simultaneously with selection (switching) of the poles.

The function of the eighth embodiment will be described next. In the coagulation mode, the high-frequency power supply 152 supplies a coagulation current to the two coagulation electrodes of the coagulation/incision treatment tool. When coagulation is complete, and the movable handle 135 is further closed to incise tissue, the switch 154 is pressed and turned on, as in the seventh embodiment. At this time, the high-frequency power supply 152 supplies an incision current to one of the coagulation electrodes and the incision electrode.

According to the eighth embodiment, the structure of the treatment tool can be simplified by causing the power supply to switch the electrodes.

(Ninth Embodiment)

Figure 17:
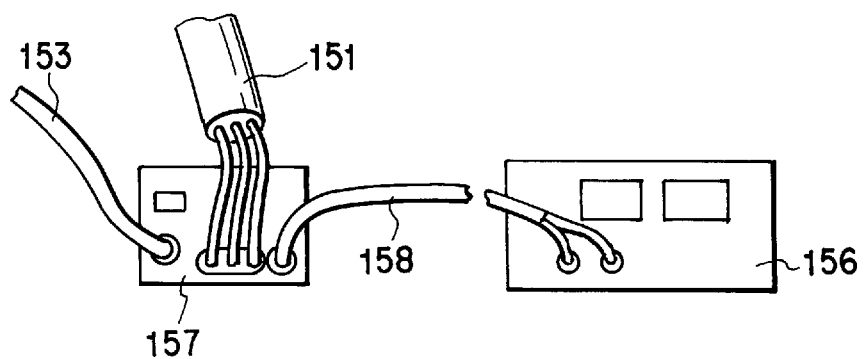
FIG. 17 is a view showing the ninth embodiment of the present invention in which the coagulation/incision treatment tool of the eighth embodiment is connected to a high-frequency power supply having general bipolar outputs (two poles)

FIG. 17 shows the ninth embodiment in which the coagulation/incision treatment tool of the eight embodiment is connected to a high-frequency power supply 156 having a general bipolar output (two poles). A bipolar coagulation/incision treatment tool 131 is connected to a pole switching unit 157 through a tripolar cable 151. The pole switching unit 157 is connected to the high-frequency power supply 156 through a bipolar cable 158. Depending on the state of a switch 154, i.e., the open/closed position of a movable handle 135, the pole switching unit 157 switches the two poles of the high-frequency power supply 156 to two of the three poles of the treatment tool. Hence, a general high-frequency power supply can be used.

(10th Embodiment)

Figure 18:
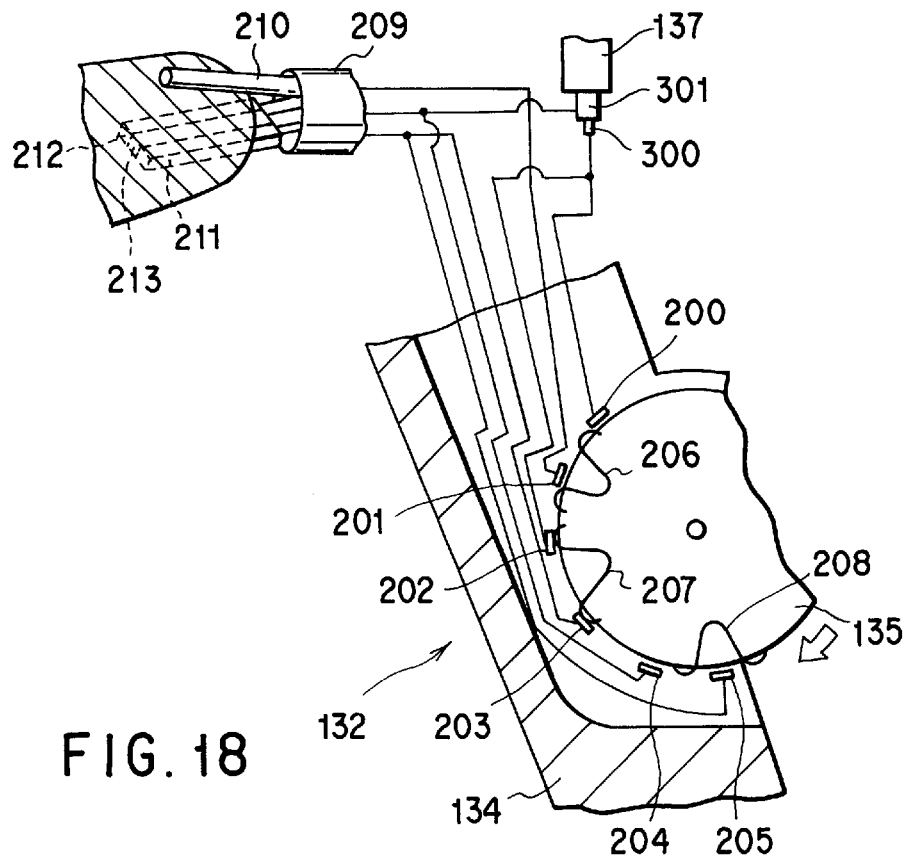
FIG. 18 is a view showing the handle portion and distal end portion of a bipolar coagulation/incision treatment tool during coagulation in the 10th embodiment of the present invention.
Figure 19:
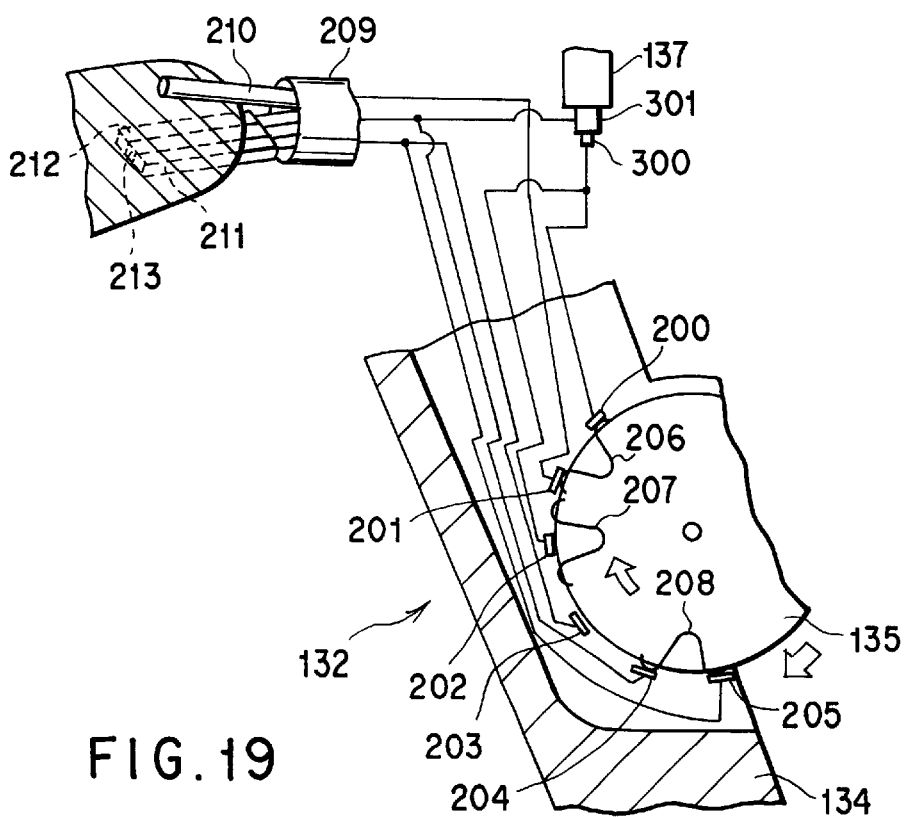
FIG. 19 is a view showing the handle portion and distal end portion of the bipolar coagulation/incision treatment tool during incision in the 10th embodiment.

FIGS. 18 and 19 show the 10th embodiment. Tripolar switching is performed in accordance with the position of a handle such that after a coagulation current is flowed across a pair of coagulation electrodes to coagulate tissue, an incision current is flowed across an incision electrode and the pair of coagulation electrodes. This tripolar switching is disclosed in the above-described DE 4032471 C2.

FIG. 18 is a longitudinal sectional view showing the handle portion and the distal end portion of a bipolar coagulation/incision treatment tool. FIG. 18 shows a state during tissue coagulation, and FIG. 19 shows a state during tissue incision . Referring to FIG. 18, a fixed handle 134 of a handle portion 132 has electrical contacts 200 to 205. A movable handle 135 has connection electrodes 206, 207, and 208 each of which connects a pair of the electrical contacts.

A treatment tool 209 has, at its distal end, an incision electrode 210, a first coagulation electrode 211, and a second coagulation electrode 212. The first and second coagulation electrodes 211 and 212 are connected integrally through an insulating member 213. The incision electrode 210 and the first and second coagulation electrodes 211 and 212 are insulated from each other. Connection of the electrical contacts will be described. The electrical contact 200 is connected to a first pole 300 of a plug 137. The electrical contact 201 is connected to the incision electrode 210. The electrical contact 202 is connected to the first pole 300 of the plug 137. The electrical contact 203 is connected to the first coagulation electrode 211. The electrical contact 204 is connected to the second coagulation electrode 212 and a second pole 301 of the plug 137. The electrical contact 205 is connected to the first coagulation electrode 211. When the movable handle 135 is set at the position shown in FIG. 18, the connection electrode 207 connects the electrical contacts 202 and 203.

When the movable handle 135 is set at the position shown in FIG. 19, the connection electrode 206 connects the electrical contacts 200 and 201, and the connection electrode 208 connects the electrical contacts 204 and 205. The arrangement and structure of the electrical contacts 200 to 205 are merely examples. A switch 154 (not illustrated in FIG. 19) for switching the current type may be arranged.

In addition, a force buffer means such as a spring may be inserted between the movable handle 135 and the distal end portion of the treatment tool. With this arrangement, the distal end portion is not applied with a force larger than a predetermined force even when the movable handle 135 is tightly closed while grasping tissue, and damage to the tissue is prevented.

According to the above-described arrangement, when the movable handle 135 is at the position shown in FIG. 18, a bipolar coagulation current flows across the pair of coagulation electrodes 211 and 212 to coagulate tissue. When the movable handle 135 is further moved to the closing position in a direction indicated by an arrow, as shown in FIG. 19, the electrical contacts switch to flow a bipolar incision current across the incision electrode 210 and the pair of coagulation electrodes 211 and 212, so the tissue is incised. As in the first embodiment, the current type may be switched simultaneously with tripolar switching. According to the 10th embodiment, tripolar switching can be done in accordance with the position of the movable handle 135, resulting in convenience in use.

The tripolar switching scheme shown in FIG. 16 or 17 may be applied to the electrode arrangement of the 10th embodiment.

The shape and scheme of the handle, electrical contacts, and switch of the 10th embodiment are merely examples, and it will be obvious to those skilled in the art that various changes and modifications can be made without departing from the scope and spirit of the present invention.

(11th Embodiment)

The 11th embodiment of the present invention will be described below. FIGS. 20A, 20B, and 20C are views showing the overall arrangement of a tripolar high-frequency treatment tool to which the 11th embodiment of the present invention is applied. Bipolar forceps 301 as a high-frequency treatment tool comprise a long insertion portion 302 to be inserted into a body cavity of a patient, a treatment portion 303 arranged at the distal end portion of the insertion portion 302 to grasp and coagulate/incise vital tissue in the body cavity and capable of being energized, and a manipulation portion 304 coupled to the proximal end portion of the insertion portion 302.

The insertion portion 302 has a sheath 306 rotatably supported by a rotary manipulation portion 305 of the manipulation portion 304. A driving shaft 307 extending into the manipulation portion 304 is inserted into the sheath 306 to freely move back and forth. First and second jaws 308a and 308b formed from electrodes for constructing the treatment portion 303 are fixed at the distal end portion of the driving shaft 307 while being biased in a direction to open.

The manipulation portion 304 has a fixed handle 311 formed integrally with a manipulation portion main body 309 and a movable handle 313 attached to the manipulation portion main body 309 to freely pivot about a pivot pin 312. When the driving shaft 307 is moved back and forth by pivoting the movable handle 313, the first and second jaws 308a and 308b open/close. FIG. 20A shows a state wherein the first and second jaws 308a and 308b are closed. FIG. 20B shows a state wherein the first and second jaws 308a and 308b are opened.

The fixed handle 311 can have a lock member 314 as shown in FIG. 20C. The lock member 314 has a hand switch 315 as a control mechanism. A signal cable 316 connected to the hand switch 315 in the lock member 314 extends from the lock member 314.

A protrusion near the manipulation portion 304 is connected to an output connector 317 connected to the electrodes of the treatment portion 303. An output cable 318 extends from the output connector 317.

Figure 21:
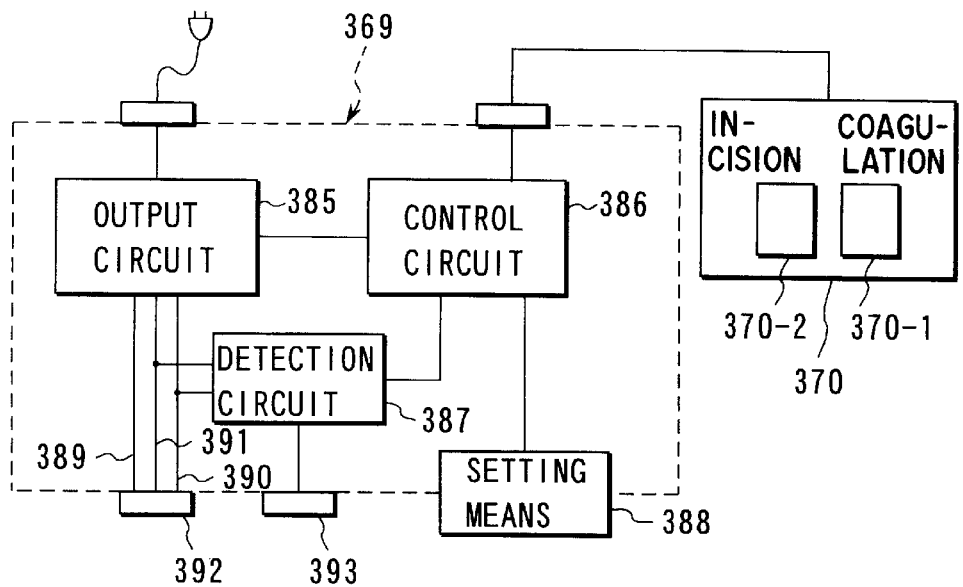
FIG. 21 is a block diagram showing the internal arrangement of a high-frequency cautery power supply unit for supplying a high-frequency current to the high-frequency treatment tool.

FIG. 21 is a block diagram showing the internal arrangement of a high-frequency cautery power supply unit 369 for supplying a high-frequency current to the above-described high-frequency treatment tool. Referring to FIG. 21, reference numeral 385 denotes an output circuit for supplying a high-frequency current; 386, a control circuit for controlling the high-frequency output from the output circuit 385 in accordance with a control signal from a foot switch 370; 388, setting means for inputting a predetermined output condition to the control circuit 386 as an electrical signal; 392, an output cable connector for connecting the output cable 318 shown in FIG. 20A; and 389, 390, and 391, lines for connecting the output circuit 385 and output cable connector 392 in correspondence with the three electrodes of the high-frequency treatment tool.

A signal cable connector 393 connects the signal cable 316 shown in FIG. 20A. A detection circuit 387 detects a high-frequency current flowing through the lines 389 to 391 and also detects a signal representing that the hand switch 315 shown in FIG. 20A is depressed and sends a detection signal to the control circuit 386. The output cable connector 392 may be formed integrally with the signal cable connector 393. In this case, the signal cable 316 of the hand switch 315 and output cable 318 are integrated.

This embodiment has three modes for treatment using the above-described high-frequency treatment tool: an automatic cut mode, a semiautomatic cut mode, and a manual mode.

In the automatic cut mode, in a series of coagulation/incision operations, the power supply unit automatically determines completion of coagulation state after the start of coagulation output, stops the coagulation operation, and then automatically switches to incision output. Switching from the coagulation operation to the incision operation can be done by, e.g., detecting a change in impedance, as in the second embodiment.

This mode is divided into a first mode in which the automatic cut operation is performed independently of the depressed switch: a coagulation switch 370-1 or an incision switch 370-2 of the foot switch 370, a second mode in which only the automatic coagulation stop operation is performed when the coagulation switch 370-1 of the foot switch 370 is depressed, and the automatic cut operation is performed when the incision switch 370-2 is depressed, and a third mode in which when the hand switch (1 button) is operated, after the coagulation operation is automatically stopped, the incision operation is automatically performed. In the automatic cut mode, operation of performing only incision is impossible. Operation of performing only coagulation is possible in the second mode.

In the semiautomatic cut mode, the apparatus notifies the user of the point of complete coagulation, and the physician determines the timing of switching from coagulation to incision. In this mode, coagulation is continuously switched to incision (there is no time lag between coagulation and incision).

When the coagulation switch 370-1 of the foot switch 370 is depressed, the coagulation operation is started. The physician is notified of the coagulation complete point. When the physician visually determines the coagulation state and operates the hand switch (1 button) while depressing the foot switch 370, the operation shifts to incision.

Instead of combinations of the hand and foot switches, a two-button hand switch may be used to perform coagulation and incision.

In the manual mode, the coagulation output and incision output are manually independently switched. The automatic stop function can be set as needed. The coagulation complete point notification function can also be set as needed. The manual mode is divided into a first mode in which both coagulation and incision are performed by operating the foot switch, a second mode in which coagulation is performed by operating the foot switch while incision is performed by operating the hand switch (1 button), a third mode in which both coagulation and incision are performed by operating the hand switch, and a fourth mode in which coagulation and incision are performed using the pressure of the handle grasped by the physician.

In all the above modes, coagulation/incision and switching to incision are easy because coagulation and incision are performed in association with the hand switch. In addition, since the semiautomatic cut mode is added to allow the physician to determine the level of coagulation, the operation can be smoothly switched to incision while reducing the risk of bleeding.

(12th Embodiment)

The 12th embodiment of the present invention will be described below. When tissue is coagulated and incised by a series of operations using only the automatic cut mode, an incision output may be generated before the tissue coagulates. Especially, since determination of coagulation varies depending on the manner of grasping tissue or thickness of tissue, hemorrhage occurs at high probability. In this embodiment, a semiautomatic cut mode and a manual mode are employed in addition to the automatic cut mode. In addition, a mode change-over switch is used to selectively switch the mode to an arbitrary one of the three modes. With this arrangement, the coagulation output can be switched to the incision output using judgement of the physician.

The mode change-over switch can be used in the following forms. As a first form, the mode change-over switch is arranged on the power supply apparatus main body, and coagulation and incision are performed using a hand switch or foot switch. As a second form, the mode change-over switch is arranged on a foot switch. As a third form, the mode change-over switch (1 button) is arranged on the handle of the high-frequency treatment tool, and coagulation and incision are performed using only a foot switch. As a fourth form, the mode change-over switch (2 buttons) is arranged on the handle of the high-frequency treatment tool, and mode switching and incision are performed using different buttons.

Figure 22:
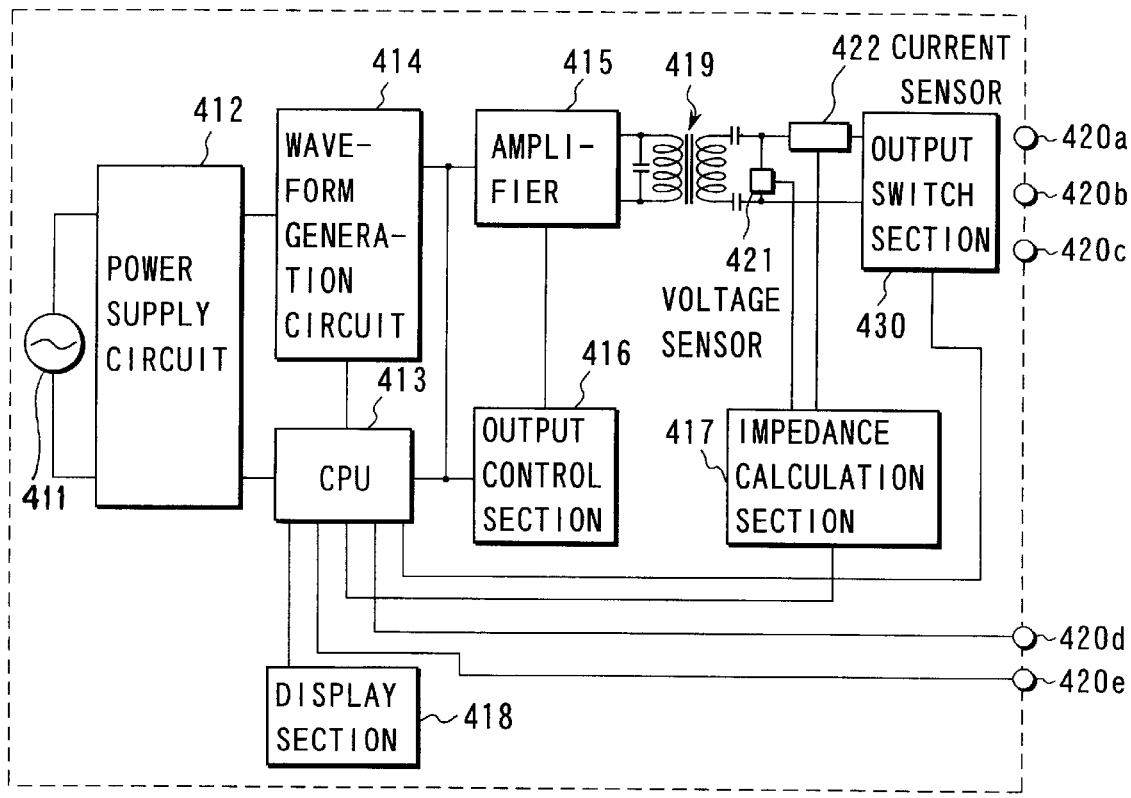
FIG. 22 is a block diagram showing the internal arrangement of a high-frequency cautery power supply unit main body according to the 12th embodiment of the present invention.

FIG. 22 is a block diagram showing the electrical arrangement of an electric knife main body according to the 12th embodiment of the present invention and the peripheral portion thereof. A power supply circuit 412 for generating desired supply power is connected to a commercial power supply 411. The power supply circuit 412 is connected to a waveform generation circuit 414 for generating a waveform corresponding to the output mode and a CPU 413 for controlling the entire power supply unit. The waveform generation circuit 414 and CPU 413 are connected to an amplifier 415 for amplifying a small signal from the waveform generation circuit 414 and an output control section 416 for controlling the output from the amplifier 415 on the basis of a control signal from the CPU 413. The primary side of an output transformer 419 is connected to the amplifier 415, and the secondary side of the output transformer 419 is connected to an output switch section 430 through a current sensor 422 and a voltage sensor 421. The output switch section 430 is connected to terminals 420a, 420b, and 420c. A high-frequency treatment tool can be connected to the terminals 420a to 420c through a tripolar cord.

The CPU 413 is connected to a display section 418, an input terminal 420d for receiving a signal for switching the mode to an arbitrary one of the automatic cut mode, semiautomatic cut mode, and mode change-over switch, and an input terminal 420e for receiving a signal from the output change-over switch for switching between the coagulation output and incision output.

Figure 23:
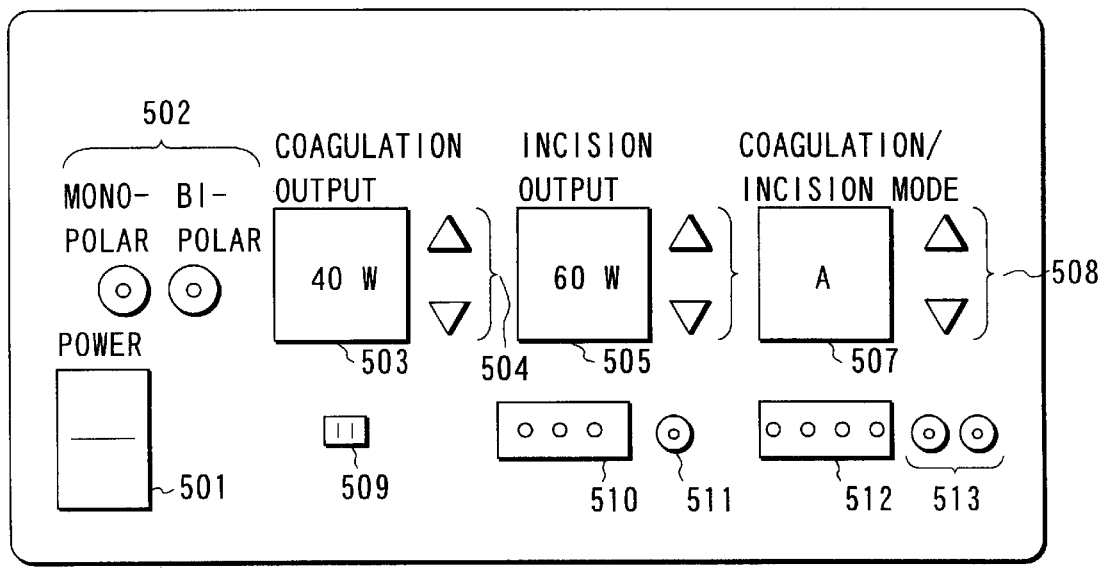
FIG. 23 is a view showing the arrangement of a front panel (output setting section) of the power supply unit main body.

FIG. 23 is a view showing the arrangement of the front panel (output setting section) of the power supply unit main body. FIG. 23 shows an example in which the mode change-over switch is arranged on the power supply unit main body. Referring to FIG. 23, reference numeral 501 denotes a power switch; 502, a switch for selecting a monopolar or bipolar output; 503, a coagulation output indicator window; 504, a coagulation output adjustment button; 505, an incision output indicator window; 506, an incision output adjustment button; and 507, a coagulation/incision mode indicator window. "A" indicates the automatic cut mode, "S" indicates the semiautomatic cut mode, and "M" indicates the manual mode. Reference numeral 508 denotes a coagulation/incision mode selection button corresponding to the mode change-over switch; 509, a P plate connector port; 510, a monopolar hand switch connector port; 511, an A cord connector port of monopolar forceps; 512, a connector port of a bipolar coagulation/incision treatment tool; and 513, an A cord connector port of the bipolar treatment tool.

Figure 24:
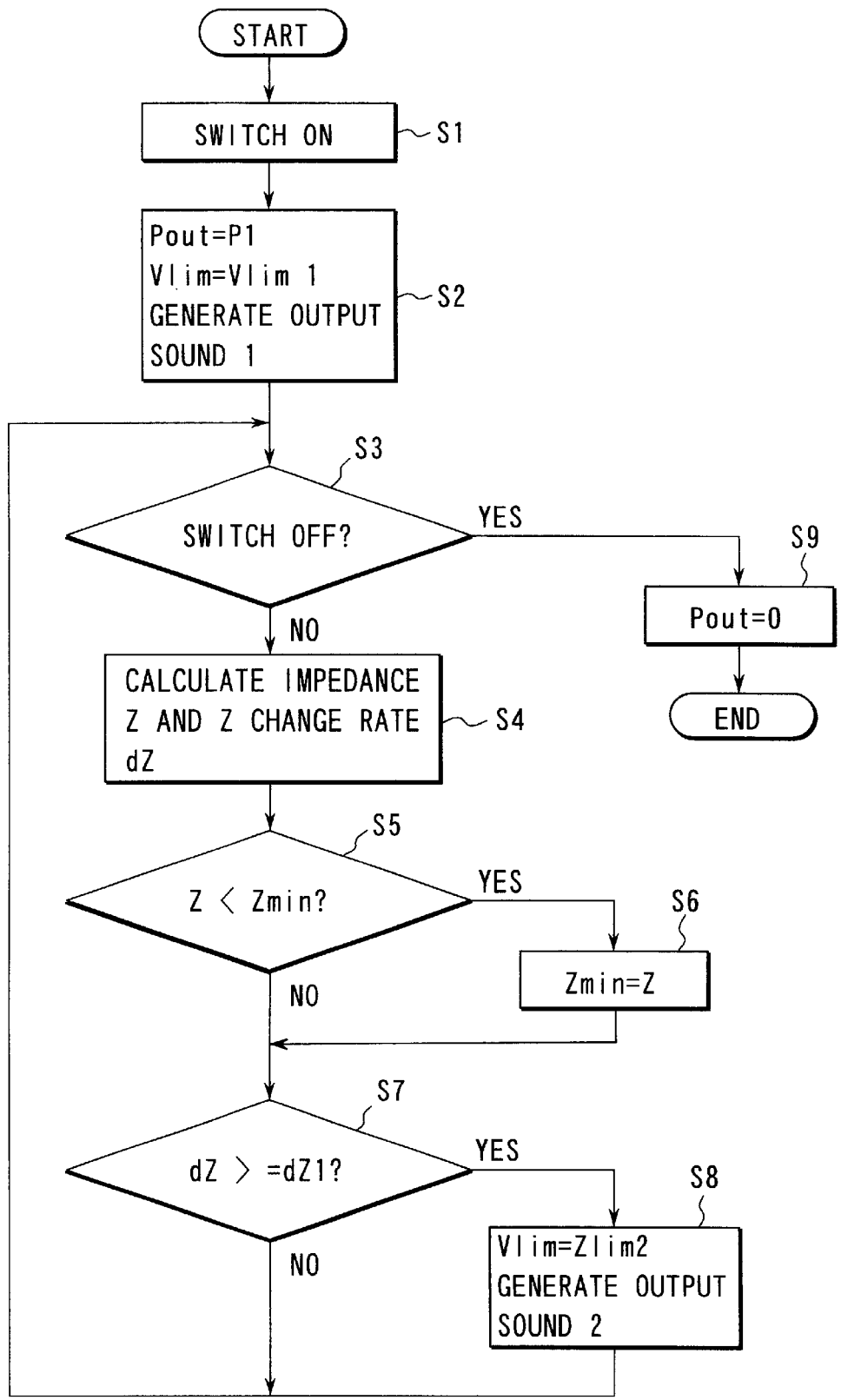
FIG. 24 is a flow chart showing details of operation in an automatic cut mode described in the 11th embodiment.

FIG. 24 is a flow chart showing details of operation in the automatic cut mode described in the 11th embodiment.

When a switch (e.g., foot switch) for starting output of the high-frequency cautery power supply unit is turned on (step S1), an output power (Pout) P1 is set to be 40 W, a voltage limiter value (Vlim) Vlim1 is set to be 60V, and coagulation output based on these set values is started in step S2. At this time, a minimum impedance value Zmin=500Ω, an impedance change rate dZ1=300Ω/sec, an output power P2=80 W, a voltage limiter value Vlim2=200V, and an impedance limiter value Zlim=500Ω are set. Also, output sound 1 is generated. The above output has output load characteristics suitable to coagulate tissue. The output has a sine waveform.

In step S3, the state of the foot switch is determined. If the foot switch is ON, the flow advances to step S4 to acquire a measured value from the voltage sensor 421 and current sensor 422 and calculate an impedance Z and an impedance change rate dZ.

In step S5, it is determined whether the calculated value of the impedance Z is smaller than the minimum value Zmin. If YES in step S5, the flow advances to step S6 to store the impedance Z as the minimum impedance value Zmin, and then the flow advances to step S7. If NO in step S5, the flow directly advances to step S7.

In step S7, it is determined whether the calculated impedance change rate dZ is equal to or smaller than the predetermined value dZ1=300Ω/sec. If YES in step S7, the flow advances to step S8 to set the voltage limiter value Vlim to be Vlim2=200V and output an incision output based on this set value. Simultaneously, output sound 2 is generated. This output has output load characteristics suitable to incise tissue. With this process, the operation shifts to incision.

If NO in step S7 or after step S8, the flow returns to step S3.

If it is determined in step S3 that the foot switch is OFF, the flow advances to step S9 to stop output (Pout=0).

Figure 25:
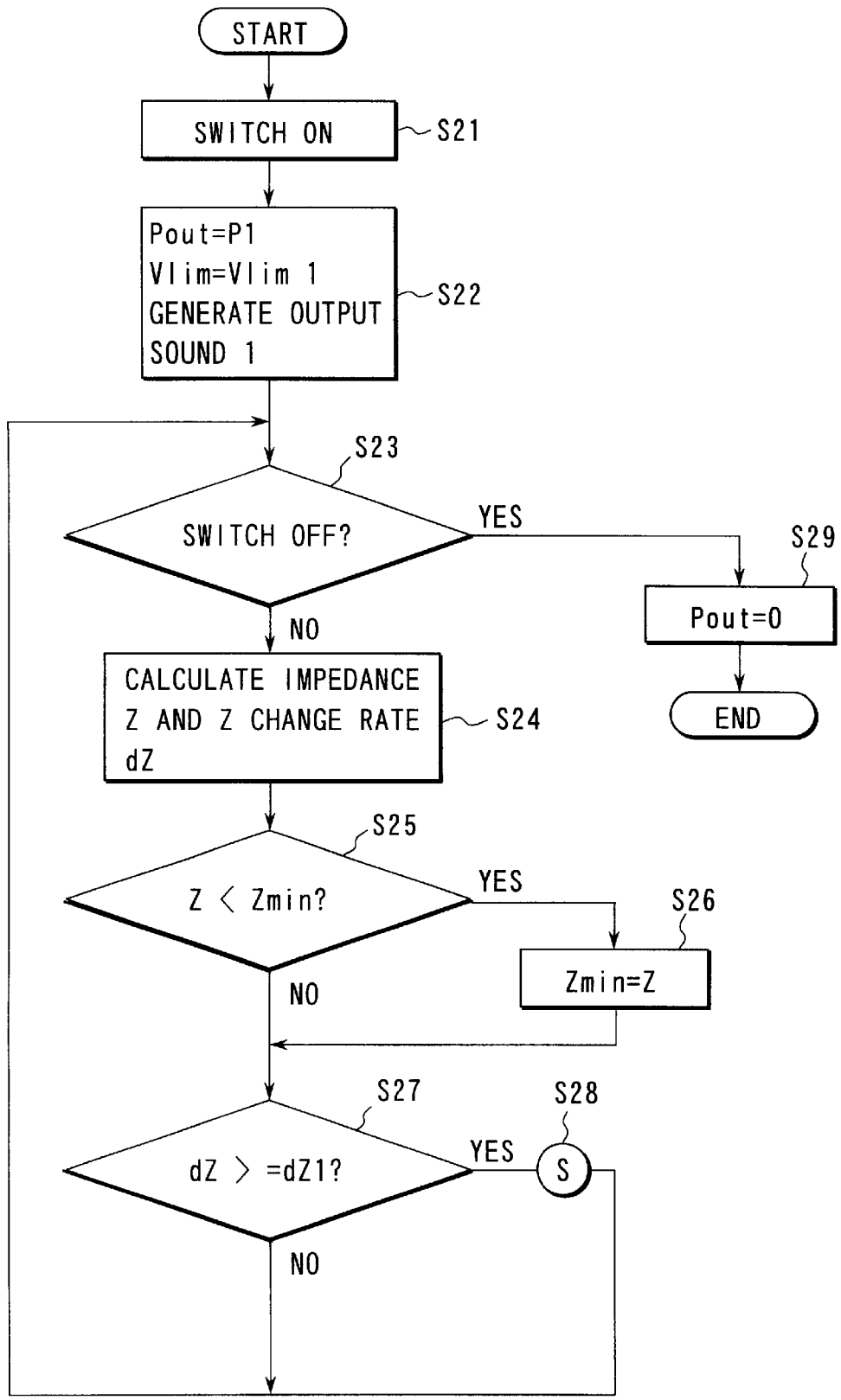
FIG. 25 is a flow chart showing details of operation in a semiautomatic cut mode described in the 11th embodiment.

FIG. 25 is a flow chart showing details of operation in the semiautomatic cut mode described in the 11th embodiment. Steps S21 to S27 and S29 of this flow except step S28 correspond to steps S1 to S7 and S9 of the flow chart shown in FIG. 24, respectively. The contents are the same as described above, and a detailed description thereof will be omitted. In step S28, the following processing is performed.

Figure 26:
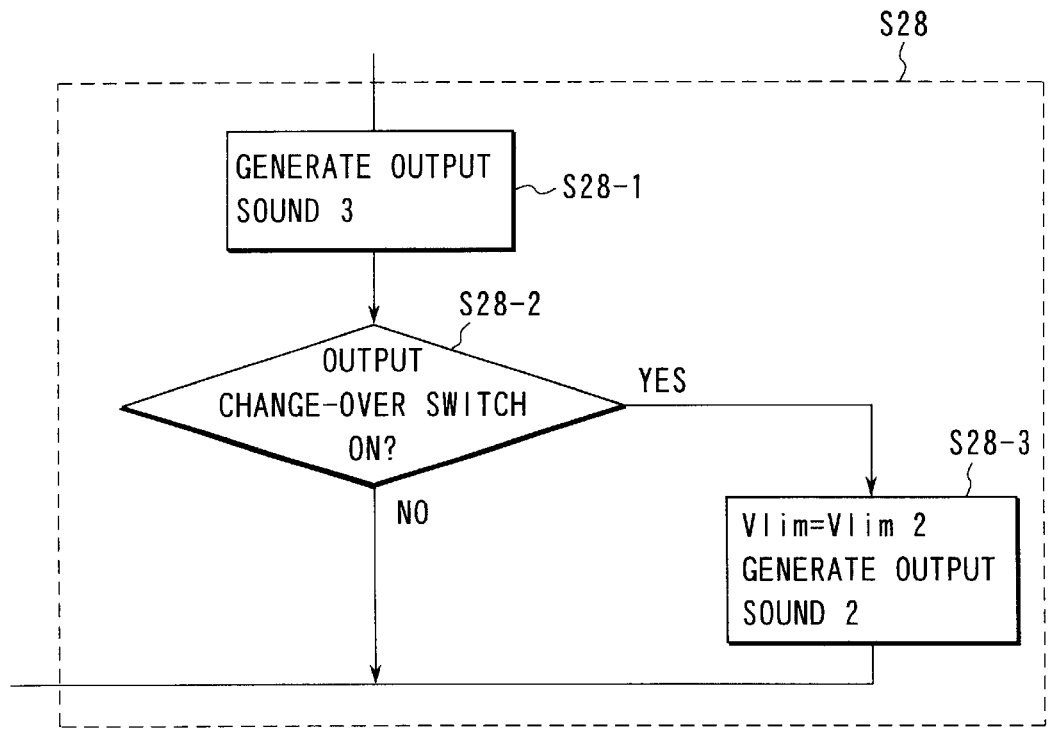
FIG. 26 is a flow chart showing details of step S28 of the flow chart shown in FIG. 25.

In step S28-1 in FIG. 26, when it is determined that coagulation is complete, output sound 3 is generated. Next, it is determined whether the output change-over switch (hand switch) is turned on (step S28-2). Output sound 3 is generated until the output change-over switch is depressed. When the physician visually determines that coagulation is complete and depresses the hand switch, it is determined in step S28-2 that the output change-over switch is turned on. The flow advances to step S28-3 to set the voltage limiter value Vlim to be Vlim2=200V and output an incision output based on this set value. Simultaneously, output sound 2 is generated. In this way, in the semiautomatic cut mode, the timing of switching the coagulation output to the incision output is determined by discretion of the physician.

According to the above embodiment, the coagulation output is switched to the incision output using judgement of the physician in all modes including the semiautomatic cut mode and manual mode. Since the operation shifts to incision after tissue sufficiently coagulates, bleeding rarely occurs. In addition, a mode preferred by the physician or a mode suitable to the current state can be selected from a plurality of modes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency treatment apparatus comprising:

a high-frequency treatment tool having, at a distal end portion, a treatment portion for coagulating or incising tissue;

a manipulation portion;

a high-frequency output power supply unit that is electrically connected to said high-frequency treatment tool and that selectively generates a high-frequency coagulation output for coagulating tissue and a high-frequency incision output for incising tissue based on a signal generated upon manipulating said manipulation portion; and a control mechanism that controls the high-frequency output power supply unit to generate the high-frequency coagulation output when the manipulation portion is in a first operation state and to generate the high-frequency incision output when the manipulation portion is in a second operation state.

2. An apparatus according to claim 1, wherein said second operation state is a state in which the manipulation portion is manipulated after said first operation state, whereby an incising operation is performed after a coagulation operation.

3. An apparatus according to claim 2, wherein said high-frequency output power supply unit comprises a detection section that detects a predetermined coagulation state, and said high-frequency output power supply unit generates the incision output in the second operation state only when the detection section detects that tissue coagulation has reached the predetermined coagulation state in the first operation state.

4. An apparatus according to claim 1, wherein said high-frequency treatment tool comprises a pair of jaws capable of being energized.

* * * * *

UNITED STATES PATENT AND TRADEMARK OFFICE
CERTIFICATE OF CORRECTION

PATENT NO. : 6,270,497 B1  Page 1 of 1
DATED : August 7, 2001
INVENTOR(S) : Naomi Sekino et al.

It is certified that error appears in the above-identified patent and that said Letters Patent is hereby corrected as shown below:

<u>Title page,</u>
Item [56], References Cited, U.S. PATENT DOCUMENTS insert
--     2,031,682     2/1936     Wappler et al.
      4,655,216     4/1987     Tischer
      5,267,998     12/1993     Hagen --; and
FOREIGN DOCUMENTS, insert
--     DE 4032471 C2     4/1992     Germany
      DE 4138116 A1     6/1993     Germany
      9-108234     4/1997     Japan
      9-173347     7/1997     Japan --.

Signed and Sealed this

Twenty-seventh Day of August, 2002

*Attest:*

*Attesting Officer*

JAMES E. ROGAN
*Director of the United States Patent and Trademark Office*